US010583285B2

(12) United States Patent
Liu et al.

(10) Patent No.: US 10,583,285 B2
(45) Date of Patent: Mar. 10, 2020

(54) METHODS OF FABRICATING A MULTI-ELECTRODE ARRAY FOR SPINAL CORD EPIDURAL STIMULATION

(71) Applicant: The Regents of the University of California, Oakland, CA (US)

(72) Inventors: Wentai Liu, Los Angeles, CA (US); Chih-Wei Chang, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 217 days.

(21) Appl. No.: 15/506,699

(22) PCT Filed: Aug. 27, 2015

(86) PCT No.: PCT/US2015/047272
§ 371 (c)(1),
(2) Date: Feb. 24, 2017

(87) PCT Pub. No.: WO2016/033372
PCT Pub. Date: Mar. 3, 2016

(65) Prior Publication Data
US 2017/0246450 A1 Aug. 31, 2017

Related U.S. Application Data

(60) Provisional application No. 62/042,672, filed on Aug. 27, 2014, provisional application No. 62/171,436, filed on Jun. 5, 2015.

(51) Int. Cl.
*H01R 43/20* (2006.01)
*A61N 1/05* (2006.01)
(Continued)

(52) U.S. Cl.
CPC ......... *A61N 1/0551* (2013.01); *A61N 1/0456* (2013.01); *A61N 1/0476* (2013.01);
(Continued)

(58) Field of Classification Search
CPC .. A61N 1/0551; A61N 1/0456; A61N 1/0476; C23C 14/5826; C23C 14/30;
(Continued)

(56) References Cited

U.S. PATENT DOCUMENTS 7,326,649 B2* 2/2008 Rodger ............... A61N 1/0551
257/737
7,672,734 B2* 3/2010 Anderson ............. A61N 1/05
607/117

(Continued)

FOREIGN PATENT DOCUMENTS

WO WO 2016/033369 A1 3/2016

OTHER PUBLICATIONS

PCT International Search Report and Written Opinion dated Dec. 3, 2015 issued in PCT/US2015/047272.
(Continued)

*Primary Examiner* — Donghai D Nguyen
(74) *Attorney, Agent, or Firm* — Tom Hunter; Weaver Austin Villeneuve & Sampson LLP

(57) ABSTRACT

In certain embodiments an electrode array for epidural stimulation of the spinal cord is provided where the array comprises a plurality of electrodes disposed on a flexible polymer substrate; said electrodes being electrically connected to one or more lead wires and/or connection points on an electrical connector; where the electrodes of said array are bonded to said polymer so that the electrodes can carry an electrical stimulation signal having a voltage, frequency, and current sufficient to provide epidural stimulation of a spinal cord and/or brain in vivo or in a physiological saline solution, without separation of all or a part of an electrode from the polymer substrate.

33 Claims, 12 Drawing Sheets

(51) Int. Cl.
  *A61N 1/04* (2006.01)
  *B05D 1/00* (2006.01)
  *C23C 14/08* (2006.01)
  *C23C 14/30* (2006.01)
  *C23C 14/58* (2006.01)

(52) U.S. Cl.
  CPC .............. *B05D 1/005* (2013.01); *C23C 14/08* (2013.01); *C23C 14/30* (2013.01); *C23C 14/5826* (2013.01)

(58) Field of Classification Search
  CPC ... C23C 14/08; B05D 1/005; Y10T 29/49126; Y10T 29/49155; Y10T 29/49204; Y10T 29/49222
  USPC ..... 29/830, 846, 874, 876, 884; 607/54, 117
  See application file for complete search history.

(56) References Cited

U.S. PATENT DOCUMENTS

| | | | |
|---|---|---|---|
| 7,937,153 B2 * | 5/2011 | Zhou | A61N 1/0543 607/54 |
| 8,271,099 B1 | 9/2012 | Swanson | |
| 8,295,936 B2 | 10/2012 | Wahlstrand et al. | |
| 8,700,145 B2 | 4/2014 | Kilgard et al. | |
| 8,750,957 B2 | 6/2014 | Tang et al. | |
| 8,805,542 B2 | 8/2014 | Tai et al. | |
| 2006/0003090 A1 | 1/2006 | Rodger et al. | |
| 2009/0157141 A1 | 6/2009 | Chiao et al. | |
| 2010/0070007 A1 | 3/2010 | Parker et al. | |
| 2011/0054579 A1 | 3/2011 | Kumar et al. | |
| 2011/0301665 A1 | 12/2011 | Mercanzini et al. | |
| 2012/0109295 A1 | 5/2012 | Fan | |
| 2012/0277834 A1 | 11/2012 | Mercanzini et al. | |
| 2012/0302821 A1 | 11/2012 | Burnett | |
| 2013/0303873 A1 | 11/2013 | Voros et al. | |
| 2013/0310911 A1 | 11/2013 | Tai et al. | |
| 2017/0246452 A1 | 8/2017 | Liu et al. | |

OTHER PUBLICATIONS

PCT International Preliminary Report on Patentability and Written Opinion dated Feb. 28, 2017 issued in PCT/US2015/047272.
PCT International Search Report and Written Opinion dated Dec. 8, 2015 issued in PCT/US2015/047268.
European Extended Search Report dated Mar. 8, 2018 issued in EP 15836264.0.

* cited by examiner

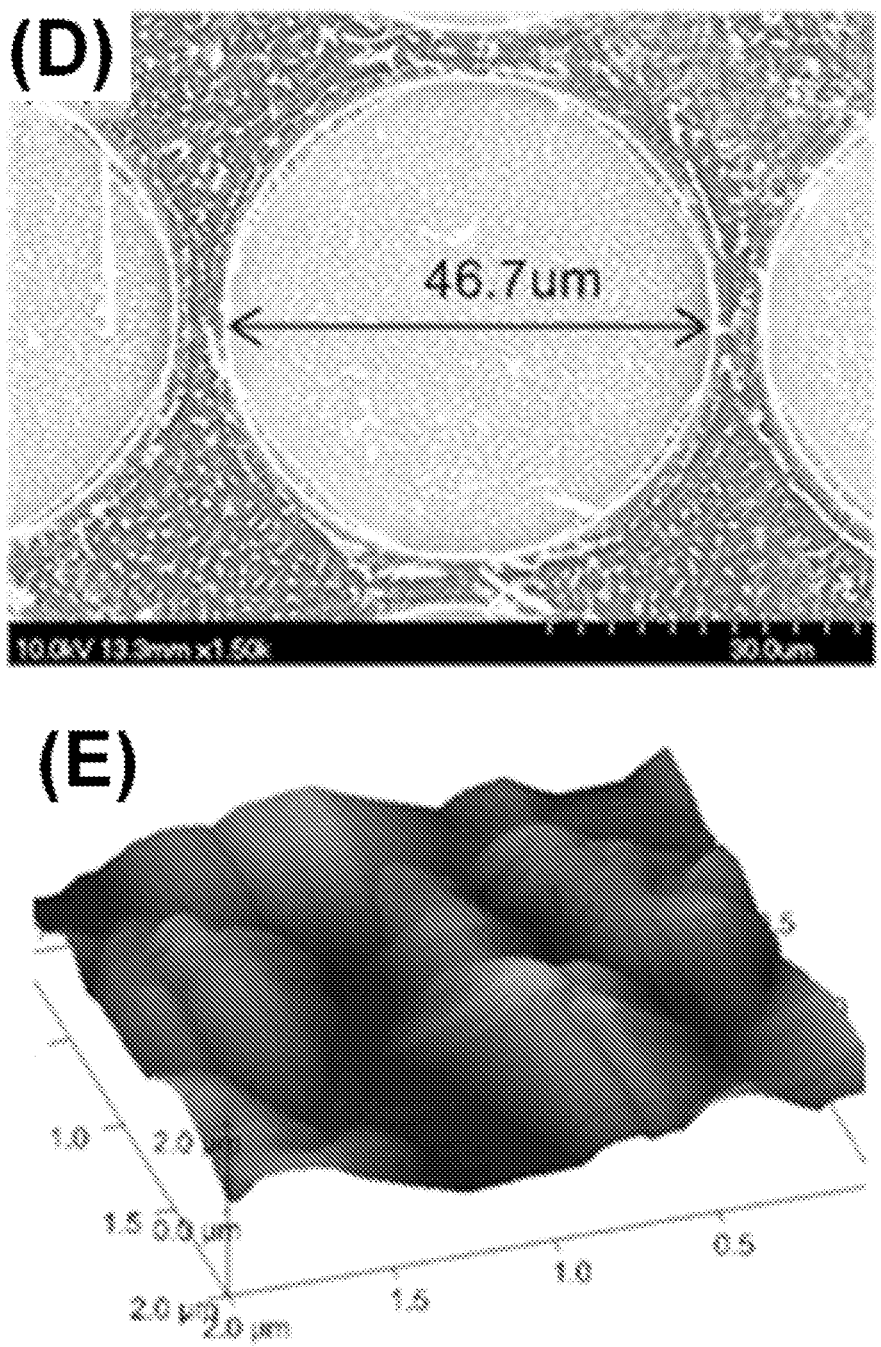
*Fig. 3, cont'd.*

METHODS OF FABRICATING A MULTI-ELECTRODE ARRAY FOR SPINAL CORD EPIDURAL STIMULATION

CROSS-REFERENCE TO RELATED APPLICATIONS

This application is a U.S. 371 National Phase of PCT/US2015/047272, filed Aug. 27, 2015, which claims benefit of and priority to U.S. Ser. No. 62/042,672, filed on Aug. 27, 2014, and to U.S. Ser. No. 62/171,436, filed on Jun. 5, 2015, all of which are incorporated herein by reference in their entirety for all purposes.

STATEMENT OF GOVERNMENTAL SUPPORT

[Not Applicable]

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

Recovery of locomotion from permanent paralysis caused by spinal cord injuries (SCI) is one of the biggest topics in spinal cord prosthesis. It is known that networks of neurons in the lumbosacral spinal cord retain an intrinsic capability to oscillate and generate coordinated rhythmic motor outputs Circuits underlying such rhythmic and oscillatory outputs are commonly referred as central pattern generators (CPGs) (Grinner (2006) *Neuron*, 52: 751-766). Studies have demonstrated that animals can regain motor control from the plasticity of the spinal cord (Lavrov et al. (2006) *J. Neurophysiol.* 96: 1699-1710), and regain movements including, but not limited to, stepping and standing by stimulating the CPGs without control from the brain (Gad et al. (2013) *J. Neuroengin. & Rehabil.*, 10: 2).

To provide the stimulus patterns into the spinal cord, various electrode arrays have been developed (see, e.g., Gad et al. (2013) *J. Neuroengin. & Rehabil.*, 10: 2; Nandra et al. (2011). *A parylene-based microelectrode array implant for spinal cord stimulation in rats,"* in *Micro Electro Mechanical Systems (MEMS)*, 2011 IEEE 24th International Conference, pp. 1007-1010).

SUMMARY

Improved electrode arrays for spinal cord stimulation are provided that enough mechanical flexibility and durability function over long time periods in vivo while delivering electrical stimulation to the spinal cord at relatively high voltage and/or current. The electrode arrays are flexible and can tolerate movements after implantation and provide selectable/programmable multi-site electrodes to obtain the optimal stimulation parameters.

Various embodiments contemplated herein may include, but need not be limited to, one or more of the following:

Embodiment 1

An electrode array for epidural stimulation of the spinal cord, said array comprising: a plurality of electrodes disposed on a flexible polymer substrate; said electrodes being electrically connected to one or more lead wires and/or connection points on an electrical connector; wherein the electrodes of said array are bonded to said polymer so that the electrodes can carry an electrical stimulation signal having a voltage, frequency, and current sufficient to provide epidural stimulation of a spinal cord and/or brain in vivo or in a physiological saline solution, without separation of all or a part of an electrode from the polymer substrate.

Embodiment 2

The electrode array of embodiment 1, wherein said array is configured so that the electrodes can carry an electrical stimulation signal having a voltage, frequency, and current sufficient to provide epidural stimulation of a spinal cord over a period of at least 1 day, or over a period of at least 3 days, or over a period of at least one week, or over a period of at least two weeks, or over a period of at least one month, or over a period of at least two months, or over a period of at least 3 months, or over a period of at least 6 months, or over a period of at least 1 year in vivo or in a physiological saline solution, without separation of all or a part of an electrode from the polymer substrate.

Embodiment 3

The electrode array according to any one of embodiments 1-2, wherein said polymer includes a polymer selected from the group consisting of polyimide, parylene, PVC, polyethylene, PEEK, polycarbonate, Ultem PEI, polysulfone, polypropylene, silicone, and polyurethane.

Embodiment 4

The electrode array of embodiment 3, wherein said polymer includes polyimide or parylene.

Embodiment 5

The electrode array according to any one of embodiments 1-4, wherein said electrodes comprise one or more metals selected from the group consisting of platinum, titanium, chromium, tungsten, gold, and/or oxides and/or alloys thereof.

Embodiment 6

The electrode array of embodiment 5, wherein said electrode array includes platinum and/or titanium.

Embodiment 7

The electrode array according to any one of embodiments 1-6, wherein said electrodes comprise two layers, each layer comprising a different metal.

Embodiment 8

The electrode array according to any one of embodiments 1-7, wherein the thickness of the electrodes or the thickness of each layer comprising the electrodes when multiple layers are present ranges from about 1 nm, or from about 2 nm or from about 5 nm, or from about 10 nm up to about 1000 nm, or up to about 800 nm, or up to about 600 nm, or up to about 500 nm, or up to about 400 nm, or up to about 300 nm, or up to about 200 nm, or up to about 100 nm.

Embodiment 9

The electrode array according to any one of embodiments 7 to 8, wherein the first layer of said electrode ranges from about 2 nm up to about 20 nm, and the second layer of said electrode ranges from about 50 nm to about 250 nm.

Embodiment 10

The electrode array of embodiment 9, wherein the first layer of said electrode is about 10 nm in thickness and the second layer of said electrode is about 200 nm in thickness.

Embodiment 11

The electrode array according to any one of embodiments 1-10, wherein each electrode comprising a plurality of electrodes comprising said array is individually connected to a corresponding connection point on an electrical connector.

Embodiment 12

The electrode array according to any one of embodiments 1-11, wherein electrodes comprising said electrode array are disposed between a said polymer substrate and a second polymer layer, said second polymer layer comprising a plurality of openings through which said electrodes are exposed.

Embodiment 13

The electrode array of embodiment 12, wherein said plurality of openings includes a regular array (columns and rows) of openings.

Embodiment 14

The electrode array of embodiment 12, wherein said plurality of openings includes an array forming an interlaced pattern of openings.

Embodiment 15

The electrode array according to any one of embodiments 12-14, wherein openings comprising said plurality of openings are substantially the same size.

Embodiment 16

The electrode array according to any one of embodiments 12-14, wherein openings comprising said plurality of openings vary in size.

Embodiment 17

The electrode array according to any one of embodiments 12-14, wherein groups of said openings are localized over each electrode.

Embodiment 18

The electrode array of embodiment 17, wherein the openings localized over each electrode comprise a large opening disposed over the electrode, surrounded by smaller openings.

Embodiment 19

The electrode array according to any one of embodiments 12-18, wherein the openings comprising said plurality of openings range in average diameter from about 2 µm up to about 500 µm, or up to about 400 µm, or up to about 300 µm, or up to about 250 µm, or up to about 100 µm, or from about 5 µm up to about 100 µm or about 80 µm or about 60 µm, or from about 10 µm up to about 50 µm, or from about 15 µm up to about 50 µm, or from about 20 µm up to about 45 µm or 50 µm, or from about 25 µm up to about 45 µm or 50 µm, or from about 30 µm up to about 45 µm or 50 µm, or from about 35 µm up to about 45 µm or 50 µm.

Embodiment 20

The electrode array according to any one of embodiments 12-19, wherein electrodes comprising said array protrude above the top surface of said second polymer layer.

Embodiment 21

The electrode array according to any one of embodiments 12-19, wherein electrodes comprising said array are disposed lower than the top surface of said second polymer layer.

Embodiment 22

The electrode array according to any one of embodiments 12-19, wherein electrodes comprising said array are substantially even with top surface of said second polymer layer.

Embodiment 23

The electrode array according to any one of embodiments 12-22, wherein a silicon dioxide layer is present on top of said second polymer layer.

Embodiment 24

The electrode array according to any one of embodiments 1-23, wherein the electrode surfaces are roughened to provide a surface area that is at least 2× the projected surface area, or at least 3× the projected surface area, or about 3.8× the projected surface area.

Embodiment 25

The electrode array according to any one of embodiments 1-24, wherein the thickness of said polymer substrate ranges from about 1 µm or from about 2 µm, or from about 5 µm up to hundreds of µm (e.g., up to about 900 µm, or up to about 800 µm, or up to about 700 µm, or up to about 600 µm, or up to about 500 µm, or up to about 400 µm, or up to about 300 µm, or up to about 200 µm, or up to about 100 µm.

Embodiment 26

The electrode array according to any one of embodiments 12-25, wherein the thickness of said second polymer substrate ranges from about 1 µm or from about 2 µm, or from about 5 µm up to hundreds of µm (e.g., up to about 900 µm, or up to about 800 µm, or up to about 700 µm, or up to about 600 µm, or up to about 500 µm, or up to about 400 µm, or up to about 300 µm, or up to about 200 µm, or up to about 100 µm.

Embodiment 27

The electrode array according to any one of embodiments 1-26, wherein said electrode array includes: a substantially continuous polyimide polymer substrate; a plurality of electrodes said electrodes comprising a first layer of titanium and a second layer of platinum disposed on top of said polymer substrate; a second polyimide polymer layer disposed on top of said electrodes, where said second polyimide layer includes a plurality of openings through which said electrodes are exposed.

Embodiment 28

The electrode array of embodiment 27, wherein said polymer substrate and said second polymer layer range in thickness from about 4 µm to about 8 µm, or from about 4 µm to about 6 µm.

Embodiment 29

The electrode array according to any one of embodiments 1-28, wherein said array includes at least about 6 different electrodes, or at least about 8 different electrodes, or at least about 12 different electrodes, or at least about 15 different electrodes, or at least about 18 different electrodes, or at least about 27 different electrodes, or at least about 36 different electrodes.

Embodiment 30

The electrode array according to any one of embodiments 1-29, wherein the electrodes comprising said array are disposed in a substantially regular array pattern.

Embodiment 31

The electrode array according to any one of embodiments 1-29, wherein the electrodes comprising said array are disposed in an interlaced array pattern.

Embodiment 32

The electrode array according to any one of embodiments 1-31, wherein electrodes comprising said array are spaced along a longitudinal axis by a distance ranging from about 0.5 mm up to about 6 mm, or from about 1 mm up to about 5 mm, or from about 2 mm up to about 4 mm, or by a distance of about 3 mm.

Embodiment 33

The electrode array according to any one of embodiments 1-32, wherein the contact surfaces of electrodes comprising said array, are substantially regular polygons and have an average maximum diameter ranging from about 3 µm up to about 150 µm, or from about 5 µm up to about 100 µm, or from about 5 µm up to about 80 µm, or from about 5 µm up to about 60 µm, or from about 10 µm up to about 50 µm, or from about 15 µm up to about 50 µm, or from about 20 µm up to about 45 µm or 50 µm, or from about 25 µm up to about 45 µm or 50 µm, or from about 30 µm up to about 45 µm or 50 µm, or from about 35 µm up to about 45 µm or 50 µm; or the contact surfaces of electrodes comprising said array, have a major and minor axis where the dimensions of the major and minor axis independently range from about 3 µm up to about 150 µm, or from about 5 µm up to about 100 µm, or from about 5 µm up to about 80 µm, or from about 5 µm up to about 60 µm, or from about 10 µm up to about 50 µm, or from about 15 µm up to about 50 µm, or from about 20 µm up to about 45 µm or 50 µm, or from about 25 µm up to about 45 µm or 50 µm, or from about 30 µm up to about 45 µm or 50 µm, or from about 35 µm up to about 45 µm or 50 µm.

Embodiment 34

The electrode of embodiment 33, wherein the contact surface of electrodes comprising said array is substantially rectangular.

Embodiment 35

The electrode of embodiment 34, wherein the contact surface of electrodes comprising said array is about 0.5 mm by 0.2 mm.

Embodiment 36

The electrode array according to any one of embodiments 1-35, wherein the effective area factor of electrodes comprising said array is at least about 2.

Embodiment 37

The electrode array according to any one of embodiments 1-36, wherein the impedance of said electrode array at 1 KHz is no more than about 5K ohm.

Embodiment 38

The electrode array according to any one of embodiments 1-37, wherein the phase at 1 KHz is no more than 50 degrees.

Embodiment 39

The electrode array according to any one of embodiments 1-38, wherein the DL capacitance is at least about 50 nF.

Embodiment 40

The electrode array according to any one of embodiments 1-39, wherein the CT resistance is no more than about 100K ohm.

Embodiment 41

The electrode array according to any one of embodiments 1-40, wherein the tissue resistance is no more than about 5K ohm.

Embodiment 42

The electrode array according to any one of embodiments 1-41, wherein said electrode array provides channel isolation of at least about −20 dB.

Embodiment 43

The electrode array according to any one of embodiments 1-42, wherein electrodes comprising said electrode array are spaced along a longitudinal axis by a distance ranging from about 0.2 mm up to about 15 mm, or from about 0.5 mm up to about 10 mm, or from about 0.5 mm up to about 6 mm, or from about 1 mm up to about 5 mm, or from about 2 mm up to about 4 mm, or by a distance of about 3 mm.

Embodiment 44

The electrode array according to any one of embodiments 1-43, wherein said polymer substrate includes suture holes for fastening the array to a biological tissue.

Embodiment 45

An electrode array assembly, said assembly comprising a plurality of electrode arrays according to any one of embodiments 1-44.

Embodiment 46

The assembly of embodiment 45, wherein said electrode arrays are physically coupled.

Embodiment 47

The assembly of embodiment 45, wherein said electrode arrays are electrically coupled.

Embodiment 48

A system for simulation of the spinal cord and/or brain, said system comprising: an electrode array according to any one of embodiments 1-44 or an electrode array assembly according to any one of embodiments 45-47; and an electrical stimulator configured to deliver epidural stimulation of the brain or spinal cord through one or more electrodes comprising said electrode array or electrode array assembly.

Embodiment 49

The system of embodiment 48, wherein said system is configured to provide epidural stimulation at a frequency ranging from about 0.1 Hz or from about 0.5 Hz, or from about 1 Hz, or from about 2 Hz, or from about 3 Hz, or from about 5 Hz, or from about 10 Hz up to about 100 Hz, or up to about 80 Hz, or up to about 40 Hz, or from about 0.1 Hz up to about 100 Hz, or from about 1 Hz, or from about 3 Hz or from about 5 Hz up to about 80 Hz, or from about 5 Hz up to about 30 Hz, or up to about 40 Hz, or up to about 50 Hz, or up to about 100 Hz.

Embodiment 50

The system according to any one of embodiments 48-49, wherein said system is configured to provide epidural stimulation at an amplitude ranging from 0.05 mA to about 30 mA, or from about 0.1 mA to about 20 mA, or from about 0.1 mA to about 15 mA or to about 10 mA.

Embodiment 51

The system according to any one of embodiments 48-50, wherein system is configured to provide a pulse width that ranges from about 50 µs up to about 100 µs or up to about 1000 µs, from about 150 µs up to about 600 µs, or from about 200 µs to about 500 µs, or from about 200 µs to about 450 µs, or from about 100 µs up to about 1000 µs.

Embodiment 52

The system according to any one of embodiments 48-51, wherein said system is configured to provide epidural stimulation at a frequency and amplitude sufficient to stimulate or to improve postural and/or locomotor activity and/or postural or locomotor strength.

Embodiment 53

The system according to any one of embodiments 48-52, wherein said system is configured to provide epidural stimulation at a frequency and amplitude sufficient to stimulate or to improve upper extremity motion, and/or hand motion, and/or gripping, and/or grasping, and/or reaching, and/or pulling, and/or pushing.

Embodiment 54

The system according to any one of embodiments 48-53, wherein said system is configured to provide epidural stimulation at a frequency and amplitude sufficient to stimulate or improve autonomic function.

Embodiment 55

The system according to any one of embodiments 48-54, wherein said system is configured to provide epidural stimulation at a frequency and amplitude sufficient to stimulate or improve voluntary voiding of the bladder and/or bowel, and/or return of sexual function, and/or autonomic control of cardiovascular function, and/or body temperature.

Embodiment 56

The system according to any one of embodiments 48-55, wherein said system is configured to provide epidural stimulation at a frequency and amplitude sufficient to stimulate or improve ventilation, and/or swallowing, and/or chewing, and/or speaking, and/or cognitive function.

Embodiment 57

A method of stimulating or improving postural and/or locomotor activity and/or postural or locomotor strength; and/or improving motor control and/or strength in a hand and/or upper limb of a subject with a neuromotor disorder affecting motor control of the hand and/or upper limb; and/or enabling or improving one or more functions selected from the group consisting of voluntary voiding of the bladder and/or bowel, return of sexual function, autonomic control of cardiovascular function, respiration, kidney function, digestion, and control of body temperature, in a subject having a neurologically derived paralysis, said method comprising neuromodulating the spinal cord of said subject or a region thereof by administering epidural stimulation to the spinal cord or a region thereof using an electrical stimulator electrically coupled to an electrode array according to any one of embodiments 1-44 or an electrode assembly according to any one of embodiments 45-47 implanted in the brain and/or over the spinal cord or a region thereof.

Embodiment 58

The method of embodiment 57, wherein said epidural stimulation is at a frequency ranging from about 0.1 Hz or from about 0.5 Hz, or from about 1 Hz, or from about 2 Hz, or from about 3 Hz, or from about 5 Hz, or from about 10 Hz up to about 100 Hz, or up to about 80 Hz, or up to about 40 Hz, or from about 0.1 Hz up to about 100 Hz, or from about 1 Hz, or from about 3 Hz or from about 5 Hz up to about 80 Hz, or from about 5 Hz to about 30 Hz, or to about 40 Hz, or to about 50 Hz, or up to about 100 Hz.

Embodiment 59

The method according to any one of embodiments 57-58, wherein said epidural stimulation is at an amplitude ranging from 0.05 mA to about 30 mA, or from about 0.1 mA to about 20 mA, or from about 0.1 mA to about 15 mA or to about 10 mA.

Embodiment 60

The method according to any one of embodiments 57-59, wherein said pulse width ranges from about 50 μs up to about 1000 μs, from about 150 μs up to about 600 μs, or from about 200 μs to about 500 μs, or from about 200 μs to about 450 μs, or about 100 μs up to about 1000 μs.

Embodiment 61

The method according to any one of embodiments 57-60, wherein said epidural stimulation is at a frequency and amplitude sufficient to stimulating or improving postural and/or locomotor activity and/or postural or locomotor strength.

Embodiment 62

The method according to any one of embodiments 57-61, wherein said system is configured to provide epidural stimulation at a frequency and amplitude sufficient to stimulate or to improve upper extremity motion, and/or hand motion, and/or gripping, and/or grasping, and/or reaching, and/or pulling, and/or pushing.

Embodiment 63

The method according to any one of embodiments 57-62, wherein said system is configured to provide epidural stimulation at a frequency and amplitude sufficient to stimulate or improve autonomic function.

Embodiment 64

The method according to any one of embodiments 57-63, wherein said system is configured to provide epidural stimulation at a frequency and amplitude sufficient to stimulate or improve voluntary voiding of the bladder and/or bowel, and/or return of sexual function, and/or autonomic control of cardiovascular function, and/or body temperature.

Embodiment 65

The method according to any one of embodiments 57-64, wherein said system is configured to provide epidural stimulation at a frequency and amplitude sufficient to stimulate or improve ventilation, and/or swallowing, and/or chewing, and/or speaking, and/or cognitive function.

Embodiment 66

The method according to any one of embodiments 57-65, wherein said epidural stimulation is applied paraspinally over vertebrae comprising the cervical spine, brain stem, or a region thereof.

Embodiment 67

The method according to any one of embodiments 57-65, wherein said epidural stimulation is applied paraspinally vertebrae comprising the thoracic spine or a region thereof.

Embodiment 68

The method according to any one of embodiments 57-65, wherein said epidural stimulation is applied paraspinally over a region of the thoracic spine comprising T11-T12.

Embodiment 69

The method according to any one of embodiments 57-65, wherein said epidural stimulation is applied paraspinally over vertebrae comprising the lumbar spine, or lumbar sacral spine, or a region thereof.

Embodiment 70

The method according to any one of embodiments 57-65, wherein said epidural stimulation is applied paraspinally over a region of the spinal cord that controls the lower limbs or the upper limbs to stimulate or improve postural and/or locomotor activity and/or postural or locomotor strength.

Embodiment 71

The method of embodiment 70, wherein said locomotor activity includes standing and/or stepping.

Embodiment 72

The method of embodiment 70, wherein said locomotor activity includes sitting down or laying down.

Embodiment 73

The method of embodiment 70, wherein said the movement includes reaching, grasping and/or stabilizing sitting or standing posture.

Embodiment 74

The method according to any one of embodiments 57-61, wherein said method is a method of improving motor control and/or strength in a hand and/or upper limb of a subject with a neuromotor disorder affecting motor control of the hand and/or upper limb.

Embodiment 75

The method of embodiment 74, wherein said epidural stimulation is at a frequency and amplitude sufficient to improve hand strength and/or fine hand control.

Embodiment 76

The method according to any one of embodiments 74-75, wherein said epidural stimulation is applied paraspinally over the brainstem or vertebrae spanning C2 to T1.

Embodiment 77

The method according to any one of embodiments 74-75, wherein said epidural stimulation is applied paraspinally over vertebrae spanning C5 to T1.

Embodiment 78

The method according to any one of embodiments 57-77, wherein said method further includes physical training of said subject.

Embodiment 79

The method of embodiment 78, wherein said method includes subjecting said subject to physical training that exposes said subject to relevant postural, touch, movement, and/or locomotor proprioceptive signals.

Embodiment 80

The method according to any one of embodiments 78-79, wherein the combination of said stimulation and physical training modulates in real time the electrophysiological properties of spinal circuits in said subject activated by proprioceptive information derived from the region of the subject where said previously stated functions are facilitated.

Embodiment 81

The method according to any one of embodiments 78-80, wherein said physical training includes inducing a load bearing positional change in the region of the subject where locomotor activity is to be facilitated.

Embodiment 82

The method according to any one of embodiments 78-81, wherein said physical training includes movements of the lower limbs with or without resistance, and/or standing, and/or trunk control.

Embodiment 83

The method of embodiment 81, wherein the load bearing positional change in said subject includes standing.

Embodiment 84

The method of embodiment 81, wherein the load bearing positional change in said subject includes stepping.

Embodiment 85

The method of embodiment 81, wherein the load bearing positional change in said subject includes reaching.

Embodiment 86

The method of embodiment 81, wherein the load bearing positional change in said subject includes grasping and/or pulling, and/or pushing.

Embodiment 87

The method according to any one of embodiments 78-81, wherein said physical training includes hand contraction and/or upper limb movements against a resistance.

Embodiment 88

The method according to any one of embodiments 78-81, wherein said physical training includes tracing a displayed pattern by hand manipulation of a hand controller.

Embodiment 89

The method according to any one of embodiments 78-88, wherein said physical training includes robotically guided training.

Embodiment 90

The method according to any one of embodiments 78-89, wherein said physical training includes induced movement.

Embodiment 91

The method of embodiment 90, wherein said induced movement includes ventilation (induced breathing).

Embodiment 92

The method according to any one of embodiments 57-91, wherein said epidural stimulation is applied paraspinally over a region of the spinal cord that controls the bladder and/or bowel, and/or breathing, and/or sexual function, and/or chewing, and/or swallowing, and/or blood pressure, and/or body temperature, and/or digestion, and/or kidney function.

Embodiment 93

The method according to any one of embodiments 57-92, wherein one or more electrodes comprising said array are stimulated in a monopolar configuration.

Embodiment 94

The method according to any one of embodiments 57-92, wherein one or more electrodes comprising said array are stimulated in a bipolar configuration.

Embodiment 95

The method according to any one of embodiments 57-94, wherein one or more electrodes comprising said array are stimulated in a monophasic mode.

Embodiment 96

The method according to any one of embodiments 57-94, wherein one or more electrodes comprising said array are stimulated in a biphasic mode.

Embodiment 97

The method according to any one of embodiments 57-96, wherein said stimulation includes tonic stimulation.

Embodiment 98

The method according to any one of embodiments 57-97, wherein said stimulation includes simultaneous, synchronous, sequential or alternating stimulation of different spinal cord regions and/or of different electrodes or groups of electrodes.

Embodiment 99

The method according to any one of embodiments 57-98, wherein the stimulation pattern is under control of the subject.

Embodiment 100

The method according to any one of embodiments 57-99, wherein the stimulation pattern is remotely controlled wirelessly and/or over the internet (e.g., by a clinical person skilled in the art).

Embodiment 101

The method according to any one of embodiments 57-100, wherein said subject is administered at least one monoaminergic agonist.

Embodiment 102

The method of embodiment 101, wherein said at least one monoaminergic agonist includes an agent selected from the group consisting of a serotonergic drug, a dopaminergic drug, a noradrenergic drug, a GABAergic drug, and a glycinergic drug.

Embodiment 103

The method of embodiment 102, wherein said agent is selected from the group consisting of 8-hydroxy-2-(di-n-propylamino)tetralin (8-OH-DPAT), 4-(benzodioxan-5-yl)1-(indan-2-yl)piperazine (S15535), N-{2-[4-(2-methoxyphenyl)-1-piperazinyl]ethyl}-N-(2-pyridinyl)cyclohexanecarboxamide (WAY 100.635), Quipazine, Ketanserin, 4-amino-(6-chloro-2-pyridyl)-1 piperidine hydrochloride (SR 57227A), Ondanesetron, Buspirone, Methoxamine, Prazosin, Clonidine, Yohimbine, 6-chloro-1-phenyl-2,3,4,5-tetrahydro-1H-3-benzazepine-7,8-diol (SKF-81297), 7-chloro-3-methyl-1-phenyl-1,2,4,5-tetrahydro-3-benzazepin-8-ol (SCH-23390), Quinpirole, and Eticlopride.

Embodiment 104

The method of embodiment 102, wherein said monoaminergic agonist is buspirone.

Embodiment 105

The method according to any one of embodiments 57-104, wherein said subject is a non-human mammal.

Embodiment 106

The method according to any one of embodiments 57-104, wherein said subject is a human.

Embodiment 107

The method according to any one of embodiments 57-106, wherein said subject has a spinal cord injury.

Embodiment 108

The method of embodiment 107, wherein said spinal cord injury is clinically classified as motor complete.

Embodiment 109

The method of embodiment 107, wherein said spinal cord injury is clinically classified as motor incomplete.

Embodiment 110

The method according to any one of embodiments 57-105, wherein said subject has an ischemic brain injury.

Embodiment 111

The method of embodiment 110, wherein said ischemic brain injury is brain injury from stroke or acute trauma.

Embodiment 112

The method according to any one of embodiments 57-105, wherein said subject has a neurodegenerative pathology.

Embodiment 113

The method of embodiment 112, wherein said neurodegenerative pathology is associated with a condition selected from the group consisting of stroke, Parkinson's disease, Huntington's disease, Alzheimer's disease, amyotrophic lateral sclerosis (ALS), primary lateral sclerosis (PLS), dystonia, and cerebral palsy.

Embodiment 114

The method according to any one of embodiments 57-113, wherein said subject is suffering with chronic pain.

Embodiment 115

An apparatus for spinal-cord epidural stimulation, the apparatus comprising: an array of electrodes on a flexible polymer substrate; said electrode array comprising a plurality of suture holes; each electrode in the array of electrodes being individually connected to a corresponding connection point on an electrical connector; said array of electrodes configured for placement on the spinal cord and/or the brain within the epidural space; said suture holes configured to fix the array of electrodes onto the cover of the spinal cord (dura) and/or lower layer of the spinal bones.

Embodiment 116

The apparatus of embodiment 115, wherein the electrodes in the array are arranged in a matrix pattern.

Embodiment 117

The apparatus of embodiment 115, wherein the electrodes in the array are arranged in an interlaced pattern.

Embodiment 118

The apparatus of embodiment 115, wherein each electrode has a grid pattern.

Embodiment 119

The apparatus of embodiment 115, wherein each electrode has a rectangular size of approximately 0.5 mm by 0.2 mm.

Embodiment 120

The apparatus of embodiment 116, wherein: each electrode has a rectangular size of approximately 0.5 mm by 0.2 mm; each electrode is spaced apart along a longitudinal axis by approximately 3 mm; and each electrode is spaced apart along a lateral axis by approximately 1 mm.

Embodiment 121

The apparatus of embodiment 117, wherein: each electrode has a rectangular size of approximately 0.5 mm by 0.2 mm; and each electrode is spaced apart along a longitudinal axis by approximately 1.5 mm.

Embodiment 122

A method of making an electrode array for epidural stimulation of the spinal cord, said array comprising a plurality of electrodes disposed on a flexible polymer substrate, said method comprising: depositing a polymer layer on a support surface and curing said polymer layer to form a cured polymer layer; roughening the surface of said cured polymer layer; using vapor deposition and lift off to deposit metal, metal alloy, and/or metal oxide electrode layers and to define a plurality of electrodes; depositing a second polymer layer on said electrodes and curing said polymer layer to form a second cured polymer layer; depositing a silicon dioxide film on said second polymer layer and defining features in said film using a reactive ion etch with a plasma etcher; coating a positive photoresist coating onto the exposed surface; creating the electrode contact pattern using microphotolithography; using an oxygen plasma process to define the shape of the electrode array as well as exposing the contact metal layer of electrodes and connector pads; performing an oxygen/CF4 RIE to roughing the contact surface of the electrodes; and detaching the electrode array from the support surface.

Embodiment 123

The method of embodiment 122, further comprising attaching electrical correctors to the array electrodes.

Embodiment 124

The method according to any one of embodiments 122-123 further comprising silicon encapsulation of all soldered parts.

Embodiment 125

The method according to any one of embodiments 122-124, wherein said polymer includes a polymer selected from the group consisting of polyimide, parylene, PVC, polyethylene, PEEK, polycarbonate, Ultem PEI, polysulfone, polypropylene, silicone, and polyurethane

Embodiment 126

The method according to any one of embodiments 122-124, wherein said polymer includes polyimide, parylene, or silicone.

Embodiment 127

The method of embodiment 126, wherein said polymer is polyimide.

Embodiment 128

The method according to any one of embodiments 122-127, wherein the polymer layer is deposited by spin coating.

Embodiment 129

The method according to any one of embodiments 122-128, wherein said electrodes comprise a first layer of titanium underlying a second layer of platinum.

Embodiment 130

The method according to any one of embodiments 122-129, wherein said support surface includes a handle silicon wafer.

Embodiment 131

The method of embodiment 130, wherein said silicon wafer has a chromium/aluminum layer deposited thereon.

Embodiment 132

The method of embodiment 131, wherein an adhesion promoter is deposited on said chromium/aluminum layer.

Embodiment 133

The method according to any one of embodiments 122-132, wherein said roughening the surface of said cured polymer layer is by use of an oxygen-plasma process.

Embodiment 134

The method according to any one of embodiments 122-133, when complete the electrodes of said array are bonded to said polymer so that the electrodes can carry an electrical stimulation signal having a voltage, frequency, and current sufficient to provide epidural stimulation of a spinal cord and/or brain in vivo or in a physiological saline solution, without separation of all or a part of an electrode from the polymer substrate.

Embodiment 135

The method according to any one of embodiments 122-134, where when complete said array is configured so that the electrodes can carry an electrical stimulation signal having a voltage, frequency, and current sufficient to provide epidural stimulation of a spinal cord over a period of at least one week, or over a period of at least two weeks, or over a period of at least one month, or over a period of at least two months, or over a period of at least 3 months, or over a period of at least 6 months, or over a period of at least 1 year in vivo or in a physiological saline solution, without separation of all or a part of an electrode from the polymer substrate.

Embodiment 136

The method according to any one of embodiments 122-135, wherein said electrode layers comprise one or more metals selected from the group consisting of platinum, titanium, chromium, tungsten, gold, and/or oxides and/or alloys thereof.

Embodiment 137

The method of embodiment 136, wherein said electrode layers comprise platinum and/or titanium.

Embodiment 138

The method according to any one of embodiments 122-137, wherein said electrodes comprise two layers, each layer comprising a different metal.

Embodiment 139

The method according to any one of embodiments 122-138, wherein when complete the thickness of the electrodes or the thickness of each layer comprising the electrodes when multiple layers are present ranges from about 1 nm, or from about 2 nm or from about 5 nm, or from about 10 nm up to about 1000 nm, or up to about 800 nm, or up to about 600 nm, or up to about 500 nm, or up to about 400 nm, or up to about 300 nm, or up to about 200 nm, or up to about 100 nm.

Embodiment 140

The method of embodiments 138-139, wherein when complete the first layer of said electrode ranges from about 2 nm up to about 20 nm, and the second layer of said electrode ranges from about 50 nm to about 250 nm.

Embodiment 141

The method of embodiment 140, wherein when complete the first layer of said electrode is about 10 nm in thickness and the second layer of said electrode is about 200 nm in thickness.

Embodiment 142

The method according to any one of embodiments 122-141, wherein when complete each electrode comprising a plurality of electrodes comprising said array is individually connected to a corresponding connection point on an electrical connector.

Embodiment 143

The method according to any one of embodiments 122-142, wherein when complete the electrodes comprising said electrode array are disposed between said polymer substrate and a second polymer layer, said second polymer layer comprising a plurality of openings through which said electrodes are exposed.

Embodiment 144

The method of embodiment 143, wherein said plurality of openings includes a regular array (columns and rows) of openings.

Embodiment 145

The method of embodiment 143, wherein said plurality of openings includes an array forming an interlaced pattern of openings.

Embodiment 146

The method according to any one of embodiments 143-145, wherein openings comprising said plurality of openings are substantially the same size.

Embodiment 147

The method according to any one of embodiments 143-145, wherein openings comprising said plurality of openings vary in size.

Embodiment 148

The method according to any one of embodiments 143-145, wherein groups of said openings are localized over each electrode.

Embodiment 149

The method of embodiment 148, wherein the openings localized over each electrode comprise a large opening disposed over the electrode, surrounded by smaller openings.

Embodiment 150

The method according to any one of embodiments 143-149, wherein the openings comprising said plurality of openings range in average diameter from about 2 µm up to about 500 µm, or up to about 400 µm, or up to about 300 µm, or up to about 250 µm, or up to about 100 µm, or from about 5 µm up to about 100 µm or about 80 µm or about 60 µm, or from about 10 µm up to about 50 µm, or from about 15 µm up to about 50 µm, or from about 20 µm up to about 45 µm or 50 µm, or from about 25 µm up to about 45 µm or 50 µm, or from about 30 µm up to about 45 µm or 50 µm, or from about 35 µm up to about 45 µm or 50 µm.

Embodiment 151

The method according to any one of embodiments 143-150, wherein electrodes comprising said array, when complete protrude above the top surface of said second polymer layer.

Embodiment 152

The method according to any one of embodiments 143-150, wherein electrodes comprising said array when complete are disposed lower than the top surface of said second polymer layer.

Embodiment 153

The method according to any one of embodiments 143-150, wherein electrodes comprising said array when complete are substantially even with top surface of said second polymer layer.

Embodiment 154

The method according to any one of embodiments 143-153, wherein a silicon dioxide layer is present on top of said second polymer layer.

Embodiment 155

The method according to any one of embodiments 122-154, wherein the electrode surfaces are roughened to provide a surface area that is at least 2× the projected surface area, or at least 3× the projected surface area, or about 3.8× the projected surface area.

Embodiment 156

The method according to any one of embodiments 122-155, wherein the thickness of said polymer substrate ranges from about 1 µm or from about 2 µm, or from about 5 µm up to hundreds of µm (e.g., up to about 900 µm, or up to about 800 µm, or up to about 700 µm, or up to about 600 µm, or up to about 500 µm, or up to about 400 µm, or up to about 300 µm, or up to about 200 µm, or up to about 100 µm.

Embodiment 157

The method according to any one of embodiments 143-156, wherein the thickness of said second polymer substrate ranges from about 1 µm or from about 2 µm, or from about 5 µm up to hundreds of µm (e.g., up to about 900 µm, or up to about 800 µm, or up to about 700 µm, or up to about 600 µm, or up to about 500 µm, or up to about 400 µm, or up to about 300 µm, or up to about 200 µm, or up to about 100 µm.

Embodiment 158

The method according to any one of embodiments 122-157, wherein said electrode array, when complete, includes: a substantially continuous polyimide polymer substrate; a plurality of electrodes said electrodes comprising a first layer of titanium and a second layer of platinum disposed on top of said polymer substrate; a second polyimide polymer layer disposed on top of said electrodes, where said second polyimide layer includes a plurality of openings through which said electrodes are exposed.

Embodiment 159

The method of embodiment 158, wherein said polymer substrate and said second polymer layer range in thickness from about 4 µm to about 8 µm, or from about 4 µm to about 6 µm.

Embodiment 160

The method according to any one of embodiments 122-159, wherein said array includes at least about 6 different electrodes, or at least about 8 different electrodes, or at least about 12 different electrodes, or at least about 15 different electrodes, or at least about 18 different electrodes, or at least about 27 different electrodes, or at least about 36 different electrodes.

Embodiment 161

The method according to any one of embodiments 122-160, wherein the electrodes comprising said array are disposed in a substantially regular array pattern.

Embodiment 162

The method according to any one of embodiments 122-160, wherein the electrodes comprising said array are disposed in an interlaced array pattern.

Embodiment 163

The method according to any one of embodiments 122-162, wherein electrodes comprising said array are spaced along a longitudinal axis by a distance ranging from about 0.5 mm up to about 6 mm, or from about 1 mm up to about 5 mm, or from about 2 mm up to about 4 mm, or by a distance of about 3 mm.

Embodiment 164

The method according to any one of embodiments 122-163, wherein the contact surfaces of electrodes comprising said array, are substantially regular polygons and have an average maximum diameter ranging from about 3 µm up to about 150 µm, or from about 5 µm up to about 100 µm, or from about 5 µm up to about 80 µm, or from about 5 µm up to about 60 µm, or from about 10 µm up to about 50 µm, or from about 15 µm up to about 50 µm, or from about 20 µm up to about 45 µm or 50 µm, or from about 25 µm up to about 45 µm or 50 µm, or from about 30 µm up to about 45 µm or 50 µm, or from about 35 µm up to about 45 µm or 50 µm; or the contact surfaces of electrodes comprising said array, have a major and minor axis where the dimensions of the major and minor axis independently range from about 3 µm up to about 150 µm, or from about 5 µm up to about 100 µm, or from about 5 µm up to about 80 µm, or from about 5 µm up to about 60 µm, or from about 10 µm up to about 50 µm, or from about 15 µm up to about 50 µm, or from about 20 µm up to about 45 µm or 50 µm, or from about 25 µm up to about 45 µm or 50 µm, or from about 30 µm up to about 45 µm or 50 µm, or from about 35 µm up to about 45 µm or 50 µm.

Embodiment 165

The method of embodiment 164, wherein the contact surface of electrodes comprising said array is substantially rectangular.

Embodiment 166

The method of embodiment 165, wherein the contact surface of electrodes comprising said array is about 0.5 mm by 0.2 mm.

Embodiment 167

The method according to any one of embodiments 122-166, wherein, when complete, the effective area factor of electrodes comprising said array is at least about 2.

Embodiment 168

The method according to any one of embodiments 122-167, wherein, when complete, the impedance of said electrode array at 1 KHz is no more than about 5K ohm.

Embodiment 169

The method according to any one of embodiments 122-168, wherein when complete the phase of said array at 1 KHz is no more than 50 degrees.

Embodiment 170

The method according to any one of embodiments 122-169, wherein when complete the DL capacitance is at least about 50 nF.

Embodiment 171

The method according to any one of embodiments 122-170, wherein when complete the CT resistance is no more than about 100K ohm.

Embodiment 172

The method according to any one of embodiments 122-171, wherein the tissue resistance of the complete array is no more than about 5K ohm.

Embodiment 173

The method according to any one of embodiments 122-172, wherein said electrode array provides channel isolation of at least about −20 dB.

Embodiment 174

The method according to any one of embodiments 122-173, wherein electrodes comprising said electrode array are spaced along a longitudinal axis by a distance ranging from about 0.2 mm up to about 15 mm, or from about 0.5 mm up to about 10 mm, or from about 0.5 mm up to about 6 mm, or from about 1 mm up to about 5 mm, or from about 2 mm up to about 4 mm, or by a distance of about 3 mm.

Embodiment 175

The method according to any one of embodiments 122-174, wherein said polymer substrate includes suture holes for fastening the array to a biological tissue.

DEFINITIONS

As used herein "electrical stimulation" or "stimulation" means application of an electrical signal that may be either excitatory or inhibitory to a muscle, nerve, nerve body, nerve cell, neuron, and/or to groups of neurons and/or interneurons. It will be understood that an electrical signal may be applied to one or more electrodes with one or more return electrodes.

As used herein "epidural" means situated upon the dura or in very close proximity to the dura. The term "epidural stimulation" refers to electrical epidural stimulation with electrodes placed on or near the dura. In certain embodiments epidural stimulation is referred to as "electrical enabling motor control" (eEmc).

The term "motor complete" when used with respect to a spinal cord injury indicates that there is no motor function below the lesion, (e.g., no movement can be voluntarily induced in muscles innervated by spinal segments below the spinal lesion.

The term "monopolar stimulation" refers to stimulation between a local electrode and a common distant return electrode.

The term "co-administering", "concurrent administration", "administering in conjunction with" or "administering in combination" when used, for example with respect to transcutaneous electrical stimulation, epidural electrical stimulation, and pharmaceutical administration, refers to administration of the transcutaneous electrical stimulation and/or epidural electrical stimulation and/or pharmaceutical such that various modalities can simultaneously achieve a physiological effect on the subject. The administered modalities need not be administered together, either temporally or at the same site. In some embodiments, the various "treatment" modalities are administered at different times. In some embodiments, administration of one can precede administration of the other (e.g., drug before electrical stimulation or vice versa). Simultaneous physiological effect need not necessarily require presence of drug and the electrical stimulation at the same time or the presence of both stimulation modalities at the same time. In some embodiments, all the modalities are administered essentially simultaneously.

In certain embodiments cable wires are 20 mm long. Illustrative, but non-limiting connectors include the OMNETICS® A79010-001 18 pin connector, and the OMNETICS® A79034-001 36 pin connector. Suture holes can optionally be provided. In certain embodiments the suture hole ranges from 200 µm up to 800 µm, or from about 300 µm up to about 700 µm, or from about 400 µm up to about 600 µm in diameter. In certain embodiments the suture hole is about 500 µm in diameter. Illustrative, but non-limiting suture holes can be spaced about 1 to 7 mm, or about 2 to 6 mm, or about 3 to 5 mm. In certain embodiments the suture holes are 4 mm apart from each other. In certain embodiments the suture hole is at least 1 mm from the nearest electrode, or at least 2 mm from the nearest electrode, or at least 3 mm from the nearest electrode, or at least 4 mm from the nearest electrode.

Figure 10:
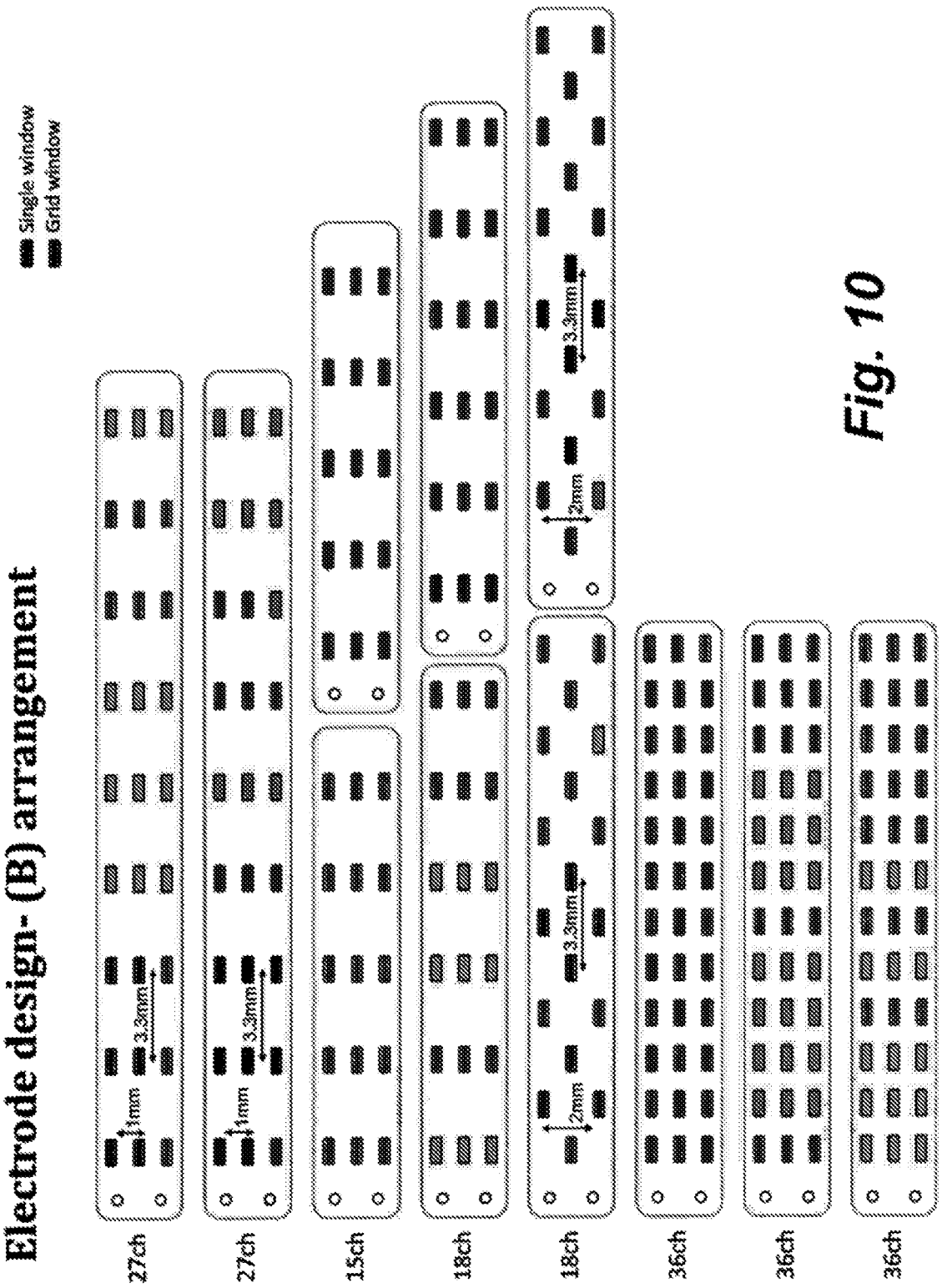

FIG. 10 shows various illustrative, but non-limiting electrode configurations.

Figure 11A:
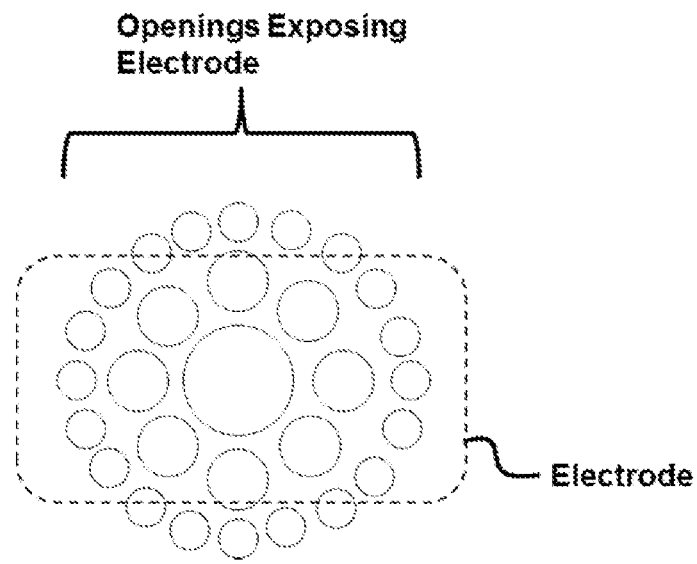
Figure 11B:
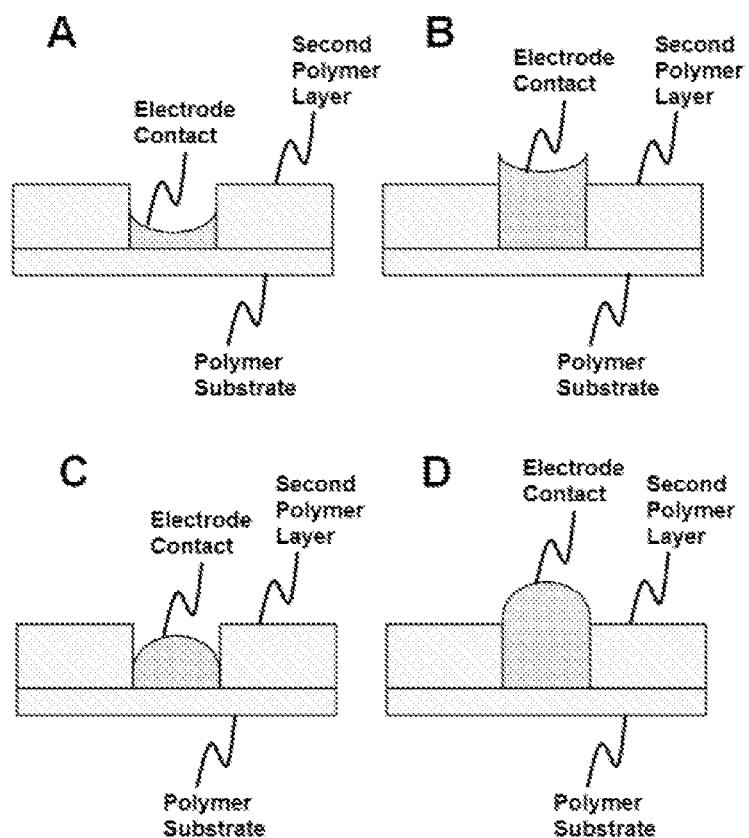

FIG. 11A illustrates one non-limiting pattern of openings in a second polymer layer where the openings vary in size and are disposed over an electrode. FIG. 11B illustrates embodiments where the electrodes comprising the electrode array protrude above the top surface of the second polymer layer (see, e.g., panels B and D), while in other embodiments the electrodes are disposed lower than the top surface of the second polymer layer (see, e.g., panels A and C), and in other embodiments, the electrodes are substantially even with top surface of the second polymer layer.

Figure 12:
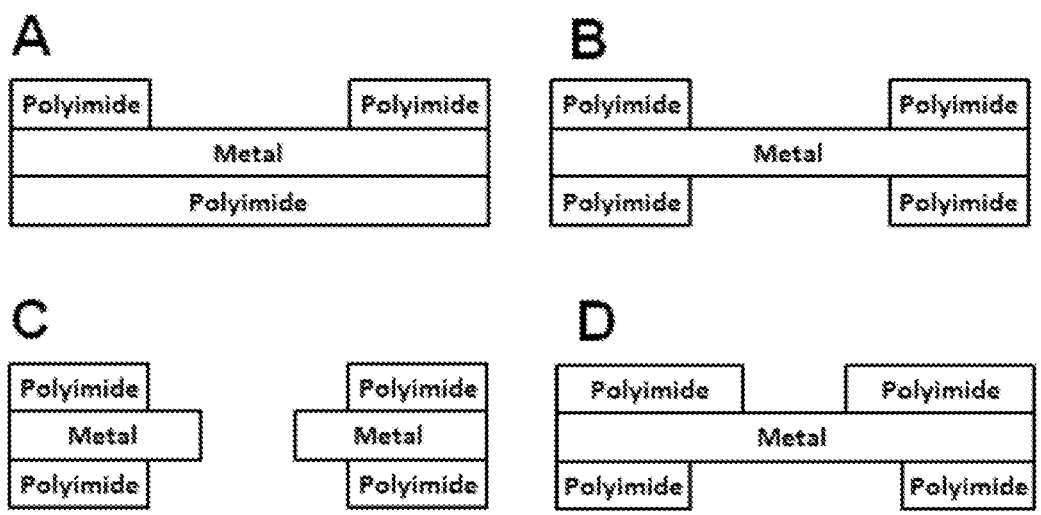

FIG. 12 schematically shows some illustrative, but non-limiting variations on patterns of electrode, polymer substrate, and second polymer layer.

Figure 13:
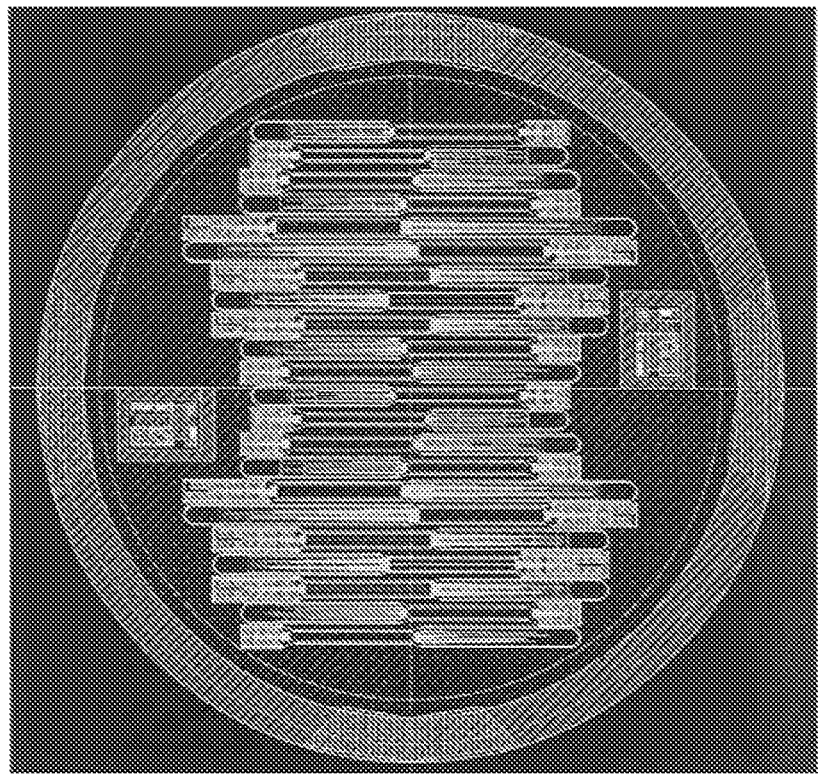

FIG. 13 illustrates one microlithography mask design example for electrode array construction. The mask shown here is used to define the geometry of layered processes described in FIG. 2. As shown, in one illustrative, but non-limiting embodiment, this design example can be fabricated on a four inch wafer (total 22 electrodes).

DETAILED DESCRIPTION

In certain embodiments novel flexible electrode arrays are provided. The electrode arrays offer a plurality of electrodes disposed on a flexible polymer substrate and can readily be utilized to deliver epidural (or other) electrical stimulation.

Unlike other polymer-based electrode arrays, the present electrode arrays are fabricated in a manner that permits the arrays to be used at high voltage and current over long periods of time without the metal electrodes separating from the polymer substrate. In particular, in various embodiments, the electrodes of the array are bonded to the polymer substrate so that the electrodes can carry an electrical stimulation signal having a voltage, frequency, and current sufficient to provide epidural stimulation of a spinal cord in vivo (or can maintain similar voltage, frequency, and current in a physiological saline solution) without separation of all or a part of an electrode from the polymer substrate. In certain embodiments the array is configured so that the electrodes can carry an electrical stimulation signal having a voltage, frequency, and current sufficient to provide epidural stimulation of a spinal cord over a period of at least one week, or over a period of at least two weeks, or over a period of at least one month, or over a period of at least two months, or over a period of at least 3 months, or over a period of at least 6 months, or over a period of at least 1 year in vivo or in a physiological saline solution, without separation of all or a part of an electrode from the polymer substrate.

Additionally, the electrode arrays offer a high double layer capacitance and therefore enhanced the charge transfer capability coupled with a low charge transfer resistance and good channel isolation. Accordingly, in view of the high mechanical stability/durability and desirable electrical characteristics, the electrode arrays described herein are well suited for prolonged in vivo use, for example, as implants to facilitate epidural stimulation of the spinal cord and/or regions thereof. The electrode arrays are well suited for use in electrical stimulation systems to provide recovery of function in subjects with a neurological impairment (e.g., subjects with brain and/or spinal cord trauma), and/or physiological impairment (e.g., subjects with bladder dysfunction).

In certain embodiments the electrode array comprises a plurality of electrodes disposed on a flexible polymer substrate, where the electrodes are electrically connected to one or more connection points on an electrical connector and electrodes comprising the array are bonded to the polymer so that the electrodes can carry an electrical stimulation signal having a voltage, frequency, and current sufficient to provide epidural stimulation of a spinal cord in vivo (or similar voltage, frequency, and current in a physiological saline solution), without separation of all or a part of an electrode from the polymer substrate.

In certain embodiments the electrode array comprises a plurality of electrodes disposed on a flexible polymer substrate, where the electrodes are electrically connected to one or more connection points on an electrical connector and electrodes comprising the array are bonded to the polymer so that the electrodes can receive an electrical signal from the spinal cord, spinal nerve, nerve root, and/or surrounding area in vivo, without separation of all or a part of the electrode from the polymer substrate.

The polymer substrate can comprise any of a number of polymers. In certain embodiments the polymers are physiologically compatible polymers and/or polymers that have been approved by the U.S. Food and Drug Administration for implantation within a human body. In certain embodiments the polymer comprises a polymer selected from the group consisting of polyimide, parylene, PVC, polyethylene, PEEK, polycarbonate, Ultem PEI, polysulfone, polypropylene, polydimethylsiloxane, silicone, and polyurethane. In certain embodiments the polymer is polyimide, parylene, or silicone. In certain embodiments the thickness of the polymer substrate ranges from about 1 µm or from about 2 µm, or from about 5 µm up to hundreds of µm (e.g., up to about 900 µm, or up to about 800 µm, or up to about 700 µm, or up to about 600 µm, or up to about 500 µm, or up to about 400 µm, or up to about 300 µm, or up to about 200 µm, or up to about 100 µm. In certain embodiments, the thickness of the polymer substrate ranges from about 1 µm, or from about 2 µm, or from about 3 µm, or from about 4 µm, or from about 5 µm up to about 100 µm, or up to about 50 µm, or up to about 40 µm, or up to about 30 µm, or up to about 20 µm, or up to about 15 µm, or up to about 10 µm, or up to about 15 µm, or up to about 20 µm, or up to about 25 µm.

In various embodiments the electrodes are fabricated from one or more electrically conductive materials, e.g., a metal, metal alloy, metal oxide, etc. In certain embodiments the electrodes comprise one or more materials selected from the group consisting of platinum, titanium, chromium, iridium, tungsten, gold, carbon-nanotubes, stainless steel, silver, silver chloride, indium tin oxide (ITO), conductive polymers (Polypyrrole (Ppy) or poly-3,4-ethylenedioxythiophene (PEDOT)) and/or their oxides and/or alloys thereof. In certain embodiments the electrodes comprises platinum and/or titanium.

In various embodiments the electrodes are fabricated from a single material layer. In certain embodiments the electrodes comprise two layers, each layer comprising a different metal, alloy, or oxide. In one illustrative, but non-limiting embodiment the electrodes comprise a layer of titanium and a layer of platinum.

In certain embodiments the thickness of the electrodes or the thickness of each layer comprising the electrodes when multiple layers are present ranges from about 1 nm, or from about 2 nm or from about 5 nm, or from about 10 nm up to about 1000 nm, or up to about 800 nm, or up to about 600 nm, or up to about 500 nm, or up to about 400 nm, or up to about 300 nm, or up to about 200 nm, or up to about 100 nm. In certain embodiments, where two layers are present, the first layer of the electrode ranges from about 1 nm up to about 1000 nm, or from about 1 nm or about 2 nm up to about 500 nm, or from about 1 nm or about 2 nm up to about 250 nm, or from about 1 nm or about 2 nm up to about 100 nm, or from about 1 or about 2 nm up to about 50 nm, or from about 1 nm or about 2 nm up to about 20 nm, and the second layer of said electrode ranges ranges from about 1 nm up to about 1000 nm, or from about 1 nm or about 2 nm up to about 500 nm, or from about 1 nm or about 2 nm up to about 250 nm, or from about 1 nm or about 2 nm up to about 100 nm, or from about 1 or about 2 nm up to about 50 nm, or from about 1 nm or about 2 nm up to about 20 nm. In certain embodiments the first layer of the electrode is about 10 nm in thickness and the second layer of said electrode is about 200 nm in thickness.

In certain embodiments each electrode comprising a plurality of electrodes comprising the array is individually connected (e.g., electrically coupled) to a corresponding connection point on an electrical connector. In certain embodiments multiple electrodes comprising the array are connected to a common connection point on an electrical connector.

In certain embodiments electrodes comprising said electrode array are disposed between the polymer substrate, and a second polymer layer, said second polymer layer comprising a plurality of openings through which the electrodes (electrode contact surfaces) are exposed. In certain embodiments the plurality of openings comprises a regular array (columns and rows) of openings or an an interlaced pattern of openings (see, e.g., FIG. 1, panel D). In certain embodiments the openings comprising the plurality of openings are substantially the same size, while in other embodiments the openings vary in size. In certain embodiments the openings are situated such that individual openings or groups of openings are localized over each electrode. In certain embodiments the openings localized over each electrode comprise a large opening disposed over the electrode, surrounded by smaller openings (see, e.g., FIG. 11A), or vice versa.

In various embodiments the openings can be shaped like substantially regular polygons (e.g., circles, squares, hexagons, etc.) while in other embodiments, the openings can be characterized by a major and minor axis (e.g., rectangles, ovoids, etc.). In certain embodiments, the openings can be irregular. In certain embodiments the openings range in average diameter (or average characteristic dimension) from about 2 µm up to about 500 µm, or up to about 400 µm, or up to about 300 µm, or up to about 250 µm, or up to about 100 µm, or from about 5 µm up to about 100 µm or about 80 µm or about 60 µm, or from about 10 µm up to about 50 µm, or from about 15 µm up to about 50 µm, or from about 20 µm up to about 45 µm or 50 µm, or from about 25 µm up to about 45 µm or 50 µm, or from about 30 µm up to about 45 µm or 50 µm, or from about 35 µm up to about 45 µm or 50 µm. In certain embodiments the major axis and minor axis independently (subject to remaining major and minor respectively) range from about 3 µm up to about 150 µm, or from about 5 µm up to about 100 µm, or from about 5 µm up to about 80 µm, or from about 5 µm up to about 60 µm, or from about 10 µm up to about 50 µm, or from about 15 µm up to about 50 µm, or from about 20 µm up to about 45 µm or 50 µm, or from about 25 µm up to about 45 µm or 50 µm, or from about 30 µm up to about 45 µm or 50 µm, or from about 35 µm up to about 45 µm or 50 µm.

In certain embodiments the electrodes comprising the electrode array protrude above the top surface of the second polymer layer (see, e.g., FIG. 11B, panels B and D), while in other embodiments the electrodes are disposed lower than the top surface of the second polymer layer (see, e.g., FIG. 11B, panels A and C), and in other embodiments, the electrodes are substantially even with top surface of the second polymer layer.

In certain embodiments a silicon dioxide layer is optionally present on top of the second polymer layer.

In certain embodiments the electrode surfaces are roughened to provide a surface area that is at least 2× the projected surface area, or at least 3× the projected surface area, or about 3.8× the projected surface area. In various embodiments the electrode surface can be convex (see, e.g., FIG. 11B, panels A and B), concave (see, e.g., FIG. 11B, panels C and D), or substantially flat.

In certain embodiments the thickness of said second polymer layer ranges about 1 µm or from about 2 µm, or from about 5 µm up to hundreds of µm (e.g., up to about 900 µm, or up to about 800 µm, or up to about 700 µm, or up to about 600 µm, or up to about 500 µm, or up to about 400 µm, or up to about 300 µm, or up to about 200 µm, or up to about 100 µm. In certain embodiments, the thickness of the polymer substrate ranges from about 1 µm, or from about 2 µm, or from about 3 µm, or from about 4 µm, or from about 5 µm up to about 100 µm, or up to about 50 µm, or up to about 40 µm, or up to about 30 µm, or up to about 20 µm, or up to about 15 µm, or up to about 10 µm, or up to about 15 µm, or up to about 20 µm, or up to about 25 µm.

In certain embodiments the electrode array comprises a substantially continuous polyimide polymer substrate; a plurality of electrodes the electrodes comprising a first layer of titanium and a second layer of platinum disposed on top of the polymer substrate; a second polyimide polymer layer disposed on top of the electrodes, where the second polyimide layer comprises a plurality of openings through which the electrodes are exposed. In certain embodiments the polymer substrate and the second polymer layer range in thickness from about 4 µm to about 8 µm, or from about 4 µm to about 6 µm.

The electrode array comprises at least 2 different electrodes or at least about 4 different electrodes, or at least about 6 different electrodes, or at least about 8 different electrodes, or at least about 12 different electrodes, or at least about 15 different electrodes, or at least about 18 different electrodes, or at least about 27 different electrodes, or at least about 36 different electrodes. In certain embodiments the electrode array comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48, or more different electrodes. In certain embodiments the electrodes comprising the array are disposed in a substantially regular array pattern or an interlaced pattern, or an irregular pattern. In certain embodiments the electrodes comprising the array are spaced along a longitudinal axis by a distance ranging from about 0.2 mm up to about 15 mm, or from about 0.5 mm up to about 10 mm, or from about 0.5 mm up to about 6 mm, or from about 1 mm up to about 5 mm, or from about 2 mm up to about 4 mm, or by a distance of about 3 mm. In certain embodiments the contact surface(s) of electrodes comprising the array are substantially rectangular or substantially circular. In certain embodiments the contact surfaces of electrodes comprising the array are about 0.5 mm by 0.2 mm.

In various embodiments the polymer substrate comprises suture holes for fastening the array to a biological tissue. "In certain embodiments the substrate comprise 2, 3, 4, 5, or 6, or more suture holes.

In certain embodiments multiple electrode arrays are used to form an electrode array assembly. In certain embodiments the electrode array assembly comprises 2, 3, 4, 5, 6, 7, 8, or more electrode arrays. In certain embodiments the electrode arrays are physically coupled. In certain embodiments the electrode arrays are electrically coupled.

It will be recognized, that while the electrode arrays illustrated herein are shown a polymer substrate and second polymer layer of approximately the same thickness, in various embodiments the polymer substrate can be thicker or thinner than the second polymer layer.

It will also be noted that the electrodes may not need to have a fixed pitch size (distance of electrode center-to-center), but can vary in electrode placement.

It will also be noted that, in certain embodiments, the polymer substrate can also contain openings, e.g., to facilitate the attachment of leads (see, e.g., FIG. 12, panels B, C, and D). FIG. 12, panel A illustrates a configuration of the electrode array of FIG. 1.

In certain embodiments the electrode array can be configured with pads that can be directly soldered with metal wires instead of using connectors.

Methods of fabricating the electrode arrays are described in Examples 1 and 2. In this regard, it is noted that among other steps, the methods involve roughening the polymer substrate before deposition of the electrode material, roughening the electrode contact area increase surface area and to improve double layer capacitance and therefore enhance the charge transfer capability, and optionally depositing a second polymer layer on top of the electrodes where the second polymer layer is provided with a plurality of openings. Without being bound to a particular theory it is believed the second polymer layer improves charge distribution around the electrode and improves the durability and mechanical stability of the electrode array.

The foregoing embodiments and the arrays shown in the Examples are intended to be illustrative and non-limiting. Using the teaching provided herein numerous other electrode arrays and electrode array assemblies having the improved durability and desirable electrical characteristics, e.g., as illustrated herein, will be available to one of skill in the art.

Uses of the Electrode Arrays.

The electrode arrays described herein find uses in a number of contexts. In general, the electrode arrays can be utilized in essentially any context where it is desired to deliver or receive an electrical stimulus, e.g., to a tissue. In certain embodiments the electrode arrays are particularly well suited for implantation into a subject, e.g., to directly stimulate muscle contractions (e.g., bladder contraction, eye blink, diaphragm contraction, etc.). However in certain embodiments, the electrode arrays are implanted into a subject to stimulate the spinal cord (or regions thereof) and thereby activate various central pattern generators and restore endogenous activation patters to stimulate or improve postural and/or locomotor activity and/or postural or locomotor strength, reaching, grasping, pushing, pulling, and/or to enabling one or more functions such as voluntary voiding of the bladder and/or bowel, sexual function, control of kidney function, cognitive function, autonomic control of cardiovascular function, breathing, chewing, swallowing, speaking, control of digestive function, control/regulation of body temperature control in a subject having a neurologically derived paralysis. The methods typically involve neuromodulating the spinal cord of the subject or a region thereof by administering epidural stimulation to the spinal cord or a region thereof using an electrical stimulator electrically coupled to an electrode array and/or an electrode array assembly described herein, where the electrode array or array assembly is implanted over the spinal cord or over one or more regions thereof, and/or overlaps a spinal nerve, nerve branch, nerve root.

Accordingly, in various embodiments methods and devices are provided to facilitate movement in a mammalian subject (e.g., a human) having spinal cord injury, brain injury, neurological disease or a physiological dysfunction. In certain embodiments the methods involve stimulating the spinal cord of the subject using an electrode array described herein where the stimulation modulates the electrophysiological properties of selected spinal circuits in the subject so they can be activated, e.g., by proprioceptive derived information and/or input from spinal and/or supraspinal nerves and nerve pathways. In various embodiments the stimulation can be accompanied by physical training (e.g., movement) of the region comprising sensory motor circuits involved in the desired motor activity. In certain embodiments, the epidural electrical stimulation is administered as described herein using parameters as described in PCT Publication Nos: WO/2012/094346 (PCT/US2012/020112).

In particular illustrative embodiments, the devices and methods described herein stimulate the spinal cord with one or more electrode arrays described herein, that modulate the proprioceptive and/or supraspinal information that controls the lower limbs during standing and/or stepping and/or the upper limbs during reaching and/or grasping conditions. This "sensory" information can guide the activation of the muscles in a coordinated manner and in a manner that accommodates the external conditions, e.g., the amount of loading, speed and direction of stepping or whether the load is equally dispersed on the two lower limbs, indicating a standing event, alternating loading indicating stepping, or sensing postural adjustments signifying the intent to reach and grasp.

Unlike approaches that involve specific stimulation of motor neurons to directly induce a movement, the methods described herein enable the spinal circuitry to control the movements. More specifically, the devices and methods described herein exploit the spinal circuitry and its ability to interpret proprioceptive and/or cutaneous information, and/or supraspinal information and/or autonomic information and to respond to that proprioceptive and/or cutaneous information in a functional way. In various embodiments this is in contrast to other approaches where the actual movement is induced/controlled by direct stimulation (e.g., of particular motor neurons and/or muscles).

In one illustrative embodiment, the subject is fitted with one or more implantable electrode arrays described herein that afford selective stimulation and control capability to select sites, mode(s), and intensity of stimulation via electrodes placed epidurally over, for example, the thoracic lumbar spinal cord and/or cervical spinal cord to facilitate movement of the arms and/or legs of individuals with a severely debilitating neuromotor disorder.

In certain embodiments the subject can receive the implant (e.g., in a standard procedure when used for pain alleviation) and typically about two weeks post implant the subject can be tested to identify the most effective subject specific stimulation paradigms for facilitation of movement (e.g., stepping and standing and/or arm and/or hand movement). In certain embodiments, using these stimulation paradigms the subject can practices standing and stepping and/or reaching or grabbing in an interactive rehabilitation program while being subject to spinal stimulation.

Depending on the site/type of injury and the motor or functional activity it is desired to facilitate particular spinal stimulation protocols include, but are not limited to specific stimulation sites along the lumbosacral and/or thoracic, cervical spinal cord and/or brainstem; specific combinations of stimulation sites along the lumbosacral and/or thoracic, cervical spinal cord, and/or brainstem; specific stimulation amplitudes; specific stimulation polarities (e.g., monopolar and bipolar stimulation modalities); specific stimulation frequencies; and/or specific stimulation pulse widths.

Epidural Stimulation of a Region of the Cervical Spine

In various embodiments, the methods described herein involve epidural electrical stimulation of the cervical spinal cord or a region of the cervical spinal cord of the subject utilizing one or more of the electrode arrays described herein. Illustrative regions include, but are not limited to, one or more regions straddling or spanning a region selected from the group consisting of C0-C1, C0-C2, C0-C3, C0-C4, C0-C5, C0-C6, C0-C7, C1-C1, C1-C2, C1-C3, C1-C4, C1-C7, C1-C6, C1-C7, C1-T1, C2-C2, C2-C3, C2-C4, C2-C5, C2-C6, C2-C7, C2-T1, C3-C3, C3-C4, C3-C5, C3-C6, C3-C7, C3-T1, C4-C4, C4-C5, C4-C6, C4-C7, C4-T1, C5-C5, C5-C6, C5-C7, C5-T1, C6-C6, C6-C7, C6-T1, C7-C7, and C7-T1.

Epidural Stimulation of a Region of the Thoracic Spine

In various embodiments, the methods described herein involve epidural electrical stimulation of the thoracic spinal cord or a region of the thoracic spinal cord of the subject utilizing one or more of the electrode arrays described herein. Illustrative regions include, but are not limited to, one or more regions straddling or spanning a region selected from the group consisting of T1-T1, T1-T2, T1-T3, T1-T4, T1-T5, T1-T6, T1-T7, T1-T8, T1-T9, T1-T10, T1-T11, T1-T12, T2-T1, T2-T2, T2-T3, T2-T4, T2-T5, T2-T6, T2-T7, T2-T8, T2-T9, T2-T10, T2-T11, T2-T12, T3-T1, T3-T2, T3-T3, T3-T4, T3-T5, T3-T6, T3-T7, T3-T8, T3-T9, T3-T10, T3-T11, T3-T12, T4-T1, T4-T2, T4-T3, T4-T4, T4-T5, T4-T6, T4-T7, T4-T8, T4-T9, T4-T10, T4-T11, T4-T12, T5-T1, T5-T2, T5-T3, T5-T4, T5- T5, T5-T6, T5-T7, T5-T8, T5-T9, T5-T10, T5-T11, T5-T12, T6-T1, T6-T2, T6-T3, T6-T4, T6-T5, T6-T6, T6-T7, T6-T8, T6-T9, T6-T10, T6-T11, T6-T12, T7-T1, T7-T2, T7-T3, T7- T4, T7-T5, T7-T6, T7-T7, T7-T8, T7-T9, T7-T10, T7-T11, T7-T12, T8-T1, T8-T2, T8-T3, T8-T4, T8-T5, T8-T6, T8-T7, T8-T8, T8-T9, T8-T10, T8-T11, T8-T12, T9-T1, T9-T2, T9- T3, T9-T4, T9-T5, T9-T6, T9-T7, T9-T8, T9-T9, T9-T10, T9-T11, T9-T12, T10-T1, T10-T2, T10-T3, T10-T4, T10-T5, T10-T6, T10-T7, T10-T8, T10-T9, T10-T10, T10-T11, T10-T12, T11-T1, T11-T2, T11-T3, T11-T4, T11-T5, T11-T6, T11-T7, T11-T8, T11-T9, T11-T10, T11-T11, T11-T12, T12-T1, T12-T2, T12-T3, T12-T4, T12-T5, T12-T6, T12-T7, T12-T8, T12-T9, T12-T10, T12-T11, T12-T12, and T12-L1.

Epidural Stimulation of the Lumbosacral Spinal Cord.

In various embodiments, the methods described herein involve epidural electrical stimulation of the lumbosacral spinal cord or a region of the lumbosacral spinal cord of the subject utilizing one or more of the electrode arrays described herein. Illustrative regions include, but are not limited to, one or more regions straddling or spanning a region selected from the group consisting of L1-L1, L1-L2, L1-L3, L1-L4, L1-L5, L1-S1, L1-S2, L1-S3, L1-S4, L1-S5, L2-L2, L2-L3, L2-L4, L2-L5, L2-S1, L2-S2, L2-S3, L2-S4, L2-S5, L3-L3, L3-L4, L3-L5, L3-S1, L3-S2, L3-S3, L3-S4, L3-S5, L4-L4, L4-L5, L4-S1, L4-S2, L4-S3, L4-S4, L4-S5, L5-L5, L5-S1, L5-S2, L5-S3, L5-S4, L5-S5, S1-S1, S1-S2, S1-S3, S1-S4, S1-S5, S2-S2, S2-S3, S2-S4, S2-S5, S3-S3, S3-S4, S3-S5, S4-S4, and S4-S5.

Epidural Stimulation Parameters.

In certain embodiments, the epidural stimulation is at a frequency ranging from about 0.1 Hz or from about 0.5 Hz, or from about 1 Hz, or from about 2 Hz, or from about 3 Hz, or from about 5 Hz, or from about 10 Hz up to about 100 Hz, or up to about 80 Hz, or up to about 40 Hz, or from about 0.1 Hz up to about 100 Hz, or from about 1 Hz, or from about 3 Hz or from about 5 Hz up to about 80 Hz, or from about 5 Hz to about 30 Hz, or to about 40 Hz, or to about 50 Hz.

In certain embodiments, the epidural stimulation is at an amplitude ranging from 0.05 mA to about 30 mA, or from about 0.1 mA to about 20 mA, or from about 0.1 mA to about 15 mA or to about 10 mA.

In certain embodiments, the pulse width ranges from about 50 µs to 100 or 150 µs to about 600 µs, or to about 1000 µs or from about 200 µs to about 500 µs, or from about 200 µs to about 450 µs.

In certain embodiments the epidural stimulation is at a frequency and amplitude sufficient to stimulate or to improve postural and/or locomotor activity and/or postural or locomotor strength.

In certain embodiments the epidural stimulation is at a frequency and amplitude sufficient to stimulate or to improve upper extremity motion, and/or hand motion, and/or gripping, and/or grasping, and/or reaching, and/or pulling, and/or pushing.

In certain embodiments the epidural stimulation is at a frequency and amplitude sufficient to stimulate or improve autonomic function.

In certain embodiments the epidural stimulation is at a frequency and amplitude sufficient to stimulate or improve voluntary voiding of the bladder and/or bowel, and/or return of sexual function, and/or autonomic control of cardiovascular function, and/or body temperature.

In certain embodiments the epidural stimulation is at a frequency and amplitude sufficient to stimulate or improve ventilation, and/or swallowing, and/or chewing, and/or speaking, and/or cognitive function.

In certain embodiments, the epidural stimulation is at a frequency and amplitude sufficient to improve hand strength and/or fine hand control. In certain embodiments the epidural stimulation is applied paraspinally over a cervical region identified above (e.g., over vertebrae spanning C2 to T1, over vertebrae spanning C5 to T1, etc.).

In certain embodiments, the epidural stimulation is applied paraspinally over a thoracic region identified above (e.g., over vertebrae spanning T11-T12).

In certain embodiments, the epidural stimulation is applied via a one or more electrode arrays described herein that have been surgically "permanently" implanted.

In certain embodiments, the epidural electrical stimulation is administered to an electrode array described herein using parameters as described in PCT Publication Nos: WO/2012/094346 (PCT/US2012/020112), and WO/2015/048563 (PCT/US2014/057886).

In certain embodiments the epidural stimulation is at a frequency and amplitude sufficient to stimulating or improving postural and/or locomotor activity and/or postural or locomotor strength, and/or reaching, grasping, pushing, pulling, In certain embodiments the epidural stimulation is at a frequency and amplitude sufficient to stimulate or facilitate voluntary voiding of the bladder and/or bowel, and/or return of sexual function, control of kidney function, cognitive function, and/or autonomic control of cardiovascular function, or breathing, chewing, swallowing, speaking, control of digestive function, and/or control/regulation of body temperature.

In certain embodiments the epidural stimulation is at a frequency and amplitude sufficient to improve hand strength and/or fine hand control. With respect to hand control, it is noted that WO/2015/048563 (PCT/US2014/057886) shows that the cervical spinal cord can be neuromodulated using two paradigms, i.e., electrically and pharmacologically. Moreover, the data presented therein indicate that non-functional networks can become engaged and progressively improve motor performance. In addition, the further improvement in hand function after withdrawing painless cutaneous Enabling motor control (pcEmc) and pharmacological Enabling motor control (fEmc) suggests that once functional connections are established they remain active. The methods described in WO/2015/048563 can be further enhanced by the use of the improved electrode arrays described herein when part of a system comprising a pulse generator such as that described in PCT US2012/030624, and the like.

Similarly WO/2012/094346 demonstrates that locomotor activity and/or strength and/or posture can be improved and/or restored by stimulation of the spinal circuitry. The methods described in WO/2012/094346 can be further enhanced by the use of the improved electrode arrays described herein.

As noted above, the electrode array may be implanted using any of a number of methods (e.g., a laminectomy procedure) well known to those of skill in the art.

In various embodiments, the arrays are operably linked to control circuitry that permits selection of electrode(s) or groups of electrodes to activate/stimulate and/or that controls frequency, and/or pulse width, and/or amplitude of stimulation. In various embodiments, the electrode selection, frequency, amplitude, and pulse width are independently selectable, e.g., at different times, different electrodes or groups of electrodes can be selected. At any time, different electrodes or groups of electrodes can provide different stimulation frequencies and/or amplitudes. In various embodiments, different electrodes or all electrodes can be operated in a monopolar mode and/or a bipolar mode, monophasic and/or biphasic using constant current or constant voltage delivery of the stimulation.

In certain embodiments, the electrodes can also be provided with implantable control circuitry and/or an implantable power source. In various embodiments, the implantable control circuitry can be programmed/reprogrammed by use of an external device (e.g., using a handheld device that communicates with the control circuitry through the skin). The programming can be repeated as often as necessary.

Any present or future developed stimulation system capable of providing an electrical signal to one or more regions of the cervical spinal cord using the electrode array(s) described herein may be used in accordance with the teachings provided herein. In various embodiments, the system may comprise an external pulse generator. In other embodiments the system may comprise an implantable pulse generator to produce a number of stimulation pulses that are sent to the a region in proximity to the cervical thoracic, lumbar, or lumbarsacral spinal cord by insulated leads coupled to the spinal cord by one or more electrodes and/or an electrode array. In certain embodiments the one or more electrodes or one or more electrodes comprising the electrode array may be attached to separate conductors included within a single lead.

Any external or implantable pulse generator may be used in accordance with the teachings provided herein. For example, one internal pulse generator may be an ITREL® II or Synergy or Restore Advanced pulse generator available from Medtronic, Inc, Advanced Neuromodulation Systems, Inc.'s GENESIS™ pulse generator, or Boston Scientific's Corporation's PRECISION™ pulse generator. One of skill in the art will recognize that the above-mentioned pulse generators may be advantageously modified to deliver therapy in accordance with the teachings provided herein.

In certain embodiments systems can employ a programmer coupled via a conductor to a radio frequency antenna. This system permits attending medical personnel to select the various pulse output options after implant using radio frequency communications. While, in certain embodiments, the system employs fully implanted elements, systems employing partially implanted elements may also be used in accordance with the teachings provided herein.

In one illustrative, but non-limiting system, a control module is operably coupled to a signal generation module and instructs the signal generation module regarding the signal to be generated. For example, at any given time or period of time, the control module may instruct the signal generation module to generate an electrical signal having a specified pulse width, frequency, intensity (current or voltage), etc. The control module may be preprogrammed prior to implantation or receive instructions from a programmer (or another source) through any known or future developed mechanism, such as telemetry. The control module may include or be operably coupled to memory to store instructions for controlling the signal generation module and may contain a processor for controlling which instructions to send to signal generation module and the timing of the instructions to be sent to signal generation module. In various embodiments, leads are operably coupled to signal generation module such that a stimulation pulse generated by signal generation module may be delivered via electrodes.

While in certain embodiments, two leads are utilized, it will be understood that any number of one or more leads may be employed. In addition, it will be understood that any number of one or more electrodes per lead may be employed. Stimulation pulses are applied to electrodes (which typically are cathodes) with respect to a return electrode (which typically is an anode) to induce a desired area of excitation of electrically excitable tissue in a region of the cervical spine. A return electrode such as a ground or other reference electrode and/or a recording electrode can be located on same lead as a stimulation electrode. However, it will be understood that a return electrode may be located at nearly any location, whether in proximity to the stimulation electrode or at a more remote part of the body, such as at a metallic case of a pulse generator. It will be further understood that any number of one or more return electrodes may be employed. For example, there can be a respective return electrode for each cathode such that a distinct cathode/anode pair is formed for each cathode.

The epidural electrode stimulation systems described herein are intended to be illustrative and non-limiting. Using the electrode arrays, fabrication methods, and teachings provided herein, alternative epidural stimulation systems and methods will be available to one of skill in the art.

Use of Neuromodulatory Agents.

In certain embodiments, the transcutaneous and/or epidural stimulation methods described herein are used in conjunction with various pharmacological agents, particularly pharmacological agents that have neuromodulatory activity (e.g., that are monoamergic). In certain embodiments, the use of various serotonergic, and/or dopaminergic, and/or noradrenergic, and/or GABAergic, and/or glycinergic drugs is contemplated. These agents can be used in conjunction with epidural stimulation and/or transcutaneous stimulation and/or physical therapy as described above. This combined approach can help to put the spinal cord (e.g., the cervical spinal cord) in an optimal physiological state for controlling a range of hand and/or upper limb movements.

In certain embodiments, the drugs are administered systemically, while in other embodiments, the drugs are administered locally, e.g., to particular regions of the spinal cord. Drugs that modulate the excitability of the spinal neuromotor networks include, but are not limited to combinations of noradrenergic, serotonergic, GABAergic, and glycinergic receptor agonists and antagonists.

Dosages of at least one drug or agent can be between about 0.001 mg/kg and about 10 mg/kg, between about 0.01 mg/kg and about 10 mg/kg, between about 0.01 mg/kg and about 1 mg/kg, between about 0.1 mg/kg and about 10 mg/kg, between about 5 mg/kg and about 10 mg/kg, between about 0.01 mg/kg and about 5 mg/kg, between about 0.001 mg/kg and about 5 mg/kg, or between about 0.05 mg/kg and about 10 mg/kg. Typically where the drug is an approved drug, it will be administered at dosage consistent with the recommended/approved dosage for that drug.

Drugs or agents can be delivery by injection (e.g., subcutaneously, intravenously, intramuscularly), orally, rectally, or inhaled.

Illustrative pharmacological agents include, but are not limited to, agonists and antagonists to one or more combinations of serotonergic: 5-HT1A, 5-HT2A, 5-HT3, and 5HT7 receptors; to noradrenergic alpha 1 and 2 receptors; and to dopaminergic D1 and D2 receptors (see, e.g., Table 1).

TABLE 1

Illustrative, but non-limiting pharmacological agents.

| Name | Target | Action | Route | Typical Dose (mg/Kg) | Typical Range (mg/kg) |
|---|---|---|---|---|---|
| Serotonergic receptor systems | | | | | |
| 8-OHDPAT | 5-HT1A7 | Agonist | S.C. | 0.05 | 0.045-0.3 |
| Way 100.635 | 5-HT1A | Antagonist | I.P. | 0.5 | 0.4-1.5 |
| Quipazine | 5-HT2A/C | Agonist | I.P. | 0.2 | 0.18-0.6 |
| Ketanserin | 5-HT2A/C | Antagonist | I.P. | 3 | 1.5-6.0 |

TABLE 1-continued

Illustrative, but non-limiting pharmacological agents.

| Name | Target | Action | Route | Typical Dose (mg/Kg) | Typical Range (mg/kg) |
|---|---|---|---|---|---|
| SR 57227A | 5-HT3 | Agonist | I.P. | 1.5 | 1.3-1.7 |
| Ondanesetron | 5-HT3 | Antagonist | I.P. | 3 | 1.4-7.0 |
| 5B269970 Buspirone | 5-HT7 | Antagonist | I.P. | 7 | 2.0-10.0 |
| Noradrenergic receptor systems | | | | | |
| Methoxamine | Alpha1 | Agonist | I.P. | 2.5 | 1.5-4.5 |
| Prazosin | Alpha1 | Antagonist | I.P. | 3 | 1.8-3.0 |
| Clonidine | Alpha2 | Agonist | I.P. | 0.5 | 0.2-1.5 |
| Yohimbine | Alpha2 | Antagonist | I.P. | 0.4 | 0.3-0.6 |
| Dopaminergic receptor systems | | | | | |
| SKF-81297 | D1-like | Agonist | I.P. | 0.2 | 0.15-0.6 |
| SCH-23390 | D1-like | Antagonist | I.P. | 0.15 | 0.1-0.75 |
| Quinipirole | D2-like | Agonist | I.P. | 0.3 | 0.15-0.3 |
| Eticlopride | D2-like | Antagonist | I.P. | 1.8 | 0.9-1.8 |

The foregoing methods are intended to be illustrative and non-limiting. Using the teachings provided herein, other methods involving epidural electrical stimulation and/or the use of neuromodulatory agents to stimulate or improve postural and/or locomotor, motor activity and/or postural or locomotor, or motor strength and/or to enabling one or more functions such as voluntary voiding of the bladder and/or bowel, sexual function, autonomic control of cardiovascular function, control/regulation of body temperature control, kidney control, control of digestion, improvement in cognitive function, and the like in a subject having a neurologically derived paralysis.

EXAMPLES

The following examples are offered to illustrate, but not to limit the claimed invention.

Example 1

Design and Fabrication of a Multi-Electrode Array for Spinal Cord Epidural Stimulation Summary of Example 1

A detailed design, fabrication, characterization and test of a flexible multi-site platinum/polyimide based electrode array for electrical epidural stimulation in spinal cord prosthesis is described in this example. Carefully designed 8.4 µm-thick structure fabrication flow achieved an electrode surface modification with 3.8 times enhanced effective surface area without extra process needed. Measured impedance and phase of two type of electrodes are 2.35±0.21 KΩ and 2.10±0.11 KΩ, −34.25±8.07° and −27.71±8.27° at 1K Hz, respectively. The fabricated arrays were then in-vitro tested by a multichannel neural stimulation system in physiological saline to validate the capability for electrical stimulation. The measured channel isolation on adjacent electrode is about −34 dB. A Randles cell model was used to investigate the charging waveforms, the model parameters were then extracted by various methods. The measured charge transfer resistance, double layer capacitance, and solution resistance are 1.9 KΩ, 220 nF and 15 KΩ, respectively. The results show that the fabricated array is applicable for electrical stimulation with well characterized parameters.

Combined with a multichannel stimulator, this system provides a full solution for versatile neural stimulation applications.

Introduction

In this example, we describe a flexible multi-site polymer electrode array for epidural spinal cord stimulation. For the selection of the materials, several design features were taken into account. Low stress thin film polyimide was chosen as electrode substrate because of its superior high mechanical strength, low moisture uptake rate, low dielectric constant property with great biocompatibility than other polymers (Walewyns (2013) *J. Micromechanics and Microengineering*, 23(9): 095021). Platinum/Titanium metal layer was selected for its high stability and biocompatibility. A roughening process was used to increase the effective surface area. This in turn lowered the electrode-electrolyte interface impedance as well as the compliance working voltage to allow the induced electrode to be operated within the water window (Merrill et al. (2005) *J. Neurosci. Meth.* 141: 171-198). Electrode density was taken into consideration when designing the array. Dense arrays provide more stimulus pattern combinations, but similar or unwanted stimulus effect may happen in the neighborhood of the stimulated electrode due to limited stimulus spatial resolution between adjacent electrodes. In vitro stimulation test of the fabricated array was demonstrated by using a multichannel stimulator in saline solution. This work also presents an electrode-electrolyte modeling via a new time-domain large signal analysis method developed by our group (Yi-Kai Lo et al. (2014) "Bio-Impedance Acquisition Technique Using Biphasic Current Stimulus Excitation for Implantable Neural Stimulator," *Conf Proc IEEE Eng Med Biol Soc.* August: 474-477). Detailed design and characterization procedures and results are described in the following sections.

Electrode Design and Fabrication

Figure 1:
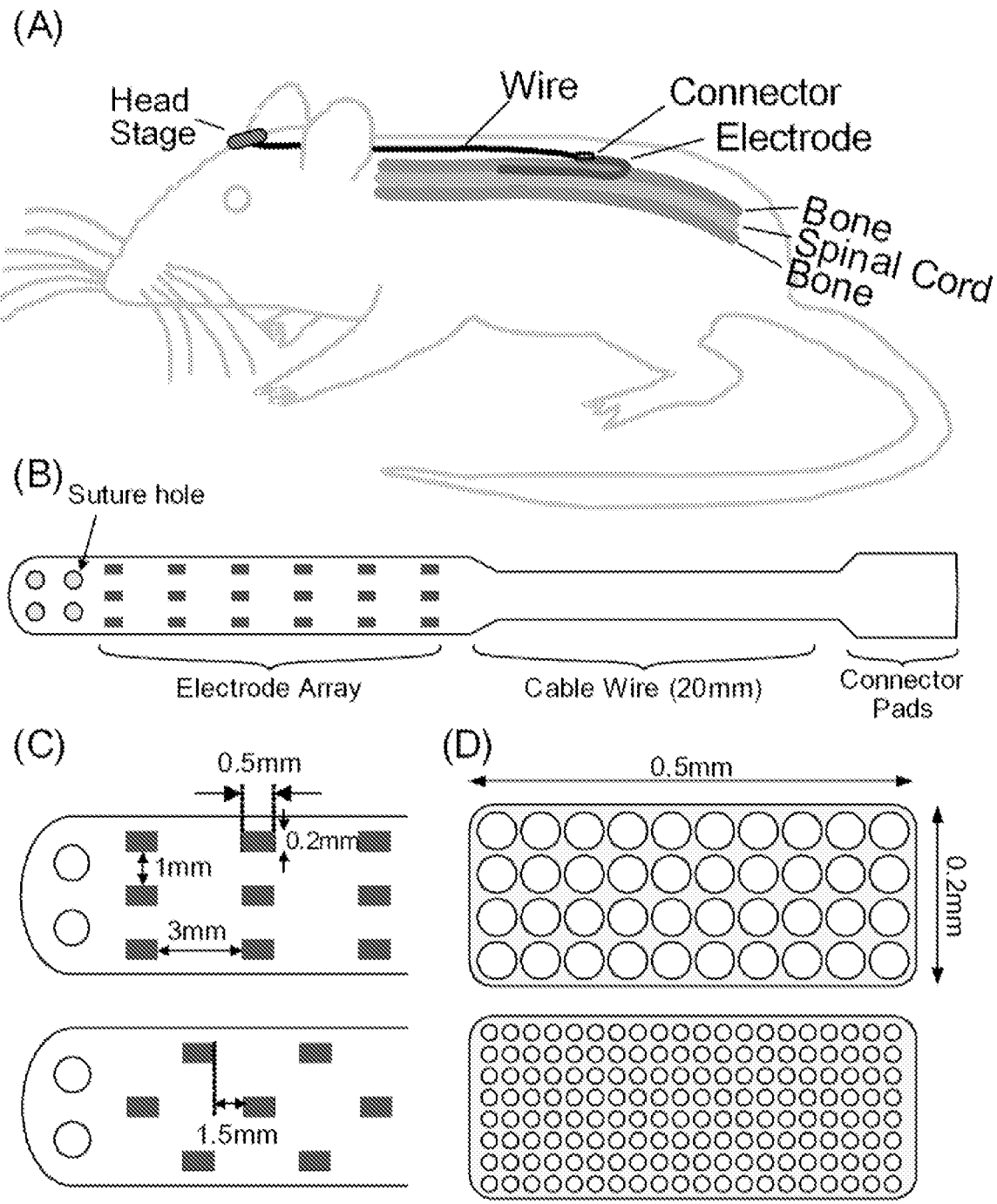
FIG. 1, panels A-D, illustrates an application site (panel A) of an implantable spinal cord prosthesis on a rat and a schematic illustration of the electrode design (panel B). the electrode design schematic. Two types of the electrode array design (panel C Upper: regular design; panel C lower: interlaced design) and two types of grid window (panel D) on the electrodes are designed for future experiments.

FIG. 1 illustrates the application goal and electrode designs. As shown in FIG. 1, panels A and B, the electrode array was designed to be placed in the epidural space between dura matter and the upper layer of the vertebrae. Suturing holes were designed on the tip (electrode end) of the array, which allows surgeons to fix the array onto the dura matter by suture. The back-end (connector end) of the electrode array can be surgically placed through the upper spinal cord and connected to lead wires to a headstage via a connector. Two types of the electrode arrangements, regular and interlaced design, and two kinds of grid window design (45 µm and 20 µm in diameter) on the electrode were designed for to provide various stimulation combinations in future animal experiments. Compared to the normal single electrode opening design (Gad et al. *Neural Engineering (NER)*, 2013 *6th International IEEE/EMBS Conference on*, 2013, pp. 319-322), the grid window designs are adapted to provide a more uniform stimulus current density and offer additional protection of the metal electrodes from peeling during the large and continuous current stimulation.

Figure 2:
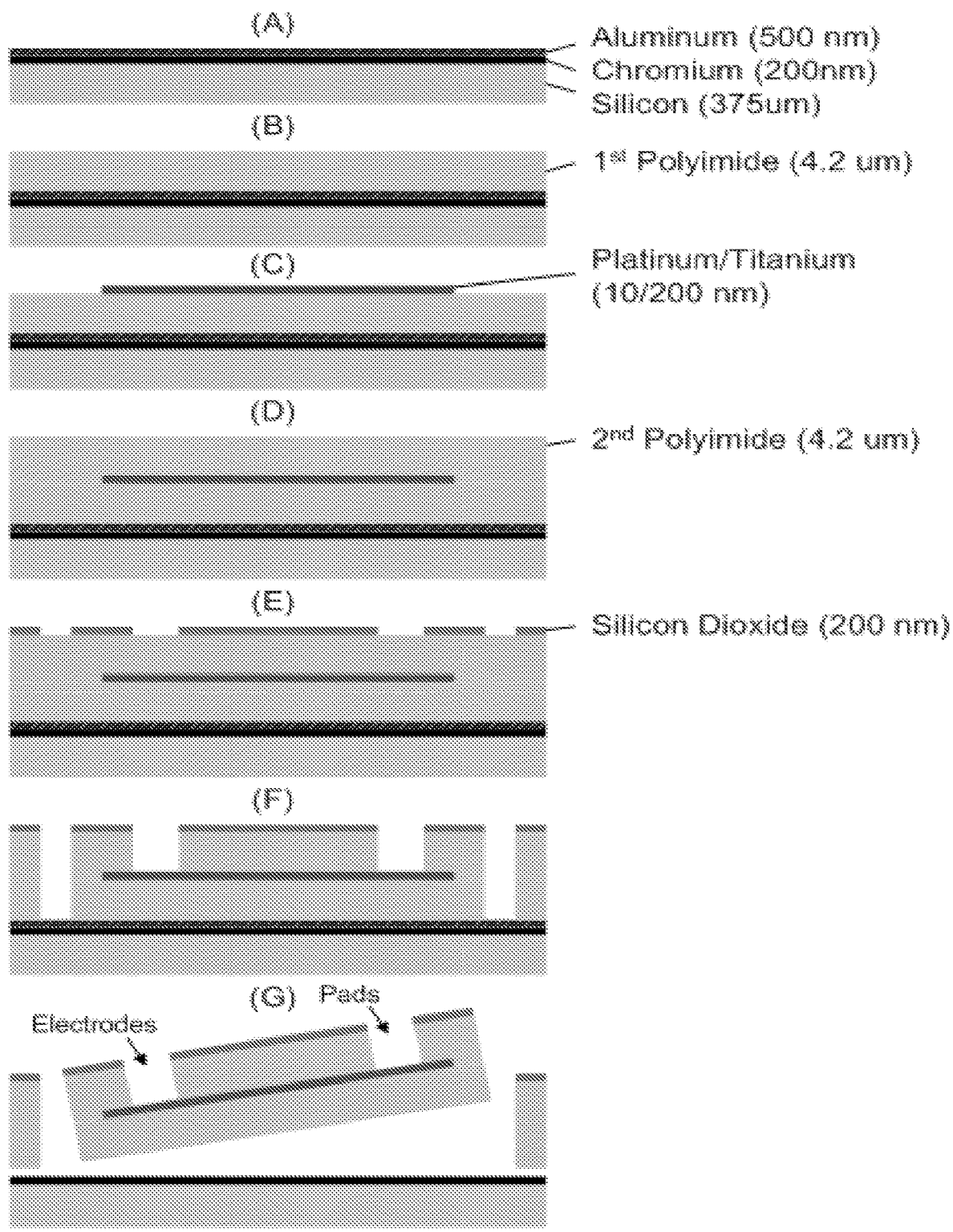
FIG. 2 schematically illustrates a process used to fabricate the flexible polymer electrode array.

FIG. 2 illustrates the fabrication process of the electrode array. (A) Chromium/Aluminum (200 nm/500 nm) layer was deposited by E-beam evaporated deposition (CHA Mark 40) on to a handle wafer. An adhesion promoter (VM-651, HD Microsystems) was applied to create a Si—C bond and provide additional adhesion for the first polyimide layer. (B) A 4.2 µm polyimide (PI-2611, HD Microsystems) was spin-coated onto the wafer, and cured in 350° C. for 30 minutes in a nitrogen-controlled oven to form full cross-link in the polyimide. (C) Titanium/Platinum (10 nm/200 nm) layer was defined and deposited using E-beam evaporated deposition (CHA Mark 40) and a lift-off technique. An oxygen-plasma roughening process was applied to the first polyimide layer for 30 seconds before the Titanium/Platinum deposition to enhance the adhesion performance. (D) Another 4.2 µm polyimide (PI-2611, HD Microsystems) was spin-coated onto the wafer, and cured in 350° C. for 30 minutes in a nitrogen-controlled oven. (E) A silicon dioxide (200 nm) film was deposited using a DC sputter (Denton Discovery-550) and defined by $CHF_3$/Ar reactive ion etch (RIE) process using a plasma etcher (Oxford Plasmalab-80 Plus). (F) A pure oxygen plasma process was used to define the array shape as well as exposing the metal layer of electrodes and connector pads. An extra oxygen/$CF_4$ RIE process was utilized to remove the residual layer composed of the silicon containing active ingredient (α-aminopropyl-triethoxysilane) which is caused by the Si—C bond promoter (Mimoun et al. (2013) *J. Vac. Sci. Technol. B*, 31: 021201). (G) Finally, the electrode arrays were detached from the handle wafer by anodic metal dissolution in a 10 wt % sodium chloride solution (Datta (1993) *IBM J. Res. Dev.* 37: 207-226). The anodic metal dissolution process dissolved the aluminum, leaving the chrome on the substrate, thus releasing the polyimide electrode arrays. After the fabrication, surface connectors (Neural Connector, Omnetics) were soldered onto the arrays. Silicone encapsulation (Sylgard 184) was then applied to seal all the soldering parts and cured in a 120° C. oven for 20 minutes to fully coagulate.

Fabrication Results and Characterization

Figure 3:
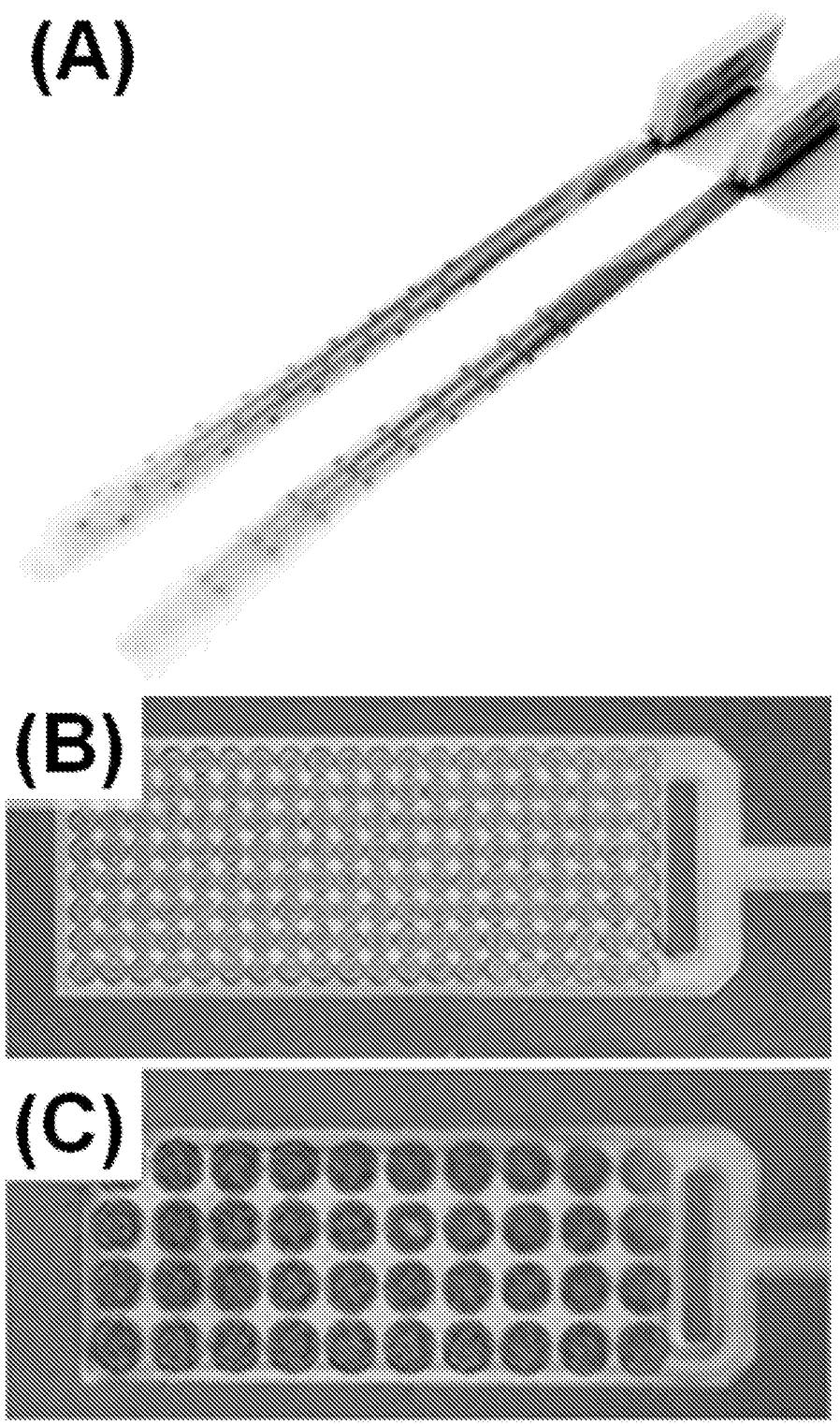
FIG. 3, panels A-E, illustrates fabrication results. Panel A: Fabricated electrode arrays soldered with connectors. Panel B: Electrode with small grid window. Panel C: Electrode with big grid window. Panel D: Scanning electron microscopy of a single grid window. Panel E: Atomic force microscopy.

FIG. 3, panels A-D, illustrates results of the fabrication process. results. FIG. 3, panel A shows fully Packaged arrays. Two types of electrode arrangement can be seen. FIG. 3, panel B, illustrates optical microscopy of the electrode with a small grid window. FIG. 3, panel C shows optical microscopy of the electrode with large grid window. Note that the platinum shows a dark color due to the roughened surface. FIG. 3, panel D shows scanning electron microscopy (SEM) of one single opening of the electrode with large grid window. The measured diameter is 46.7 µm, which is slightly larger than the original design (45 µm).

FIG. 3, panel E, shows the atomic force scanning (AFM) on a 2 µm by 2 µm area of the platinum electrode surface. The scanning was operated under tapping mode. From the AFM measurement result, the platinum film shows a roughened surface rather than a pure flat surface. The curved surface is caused by the fluorine attack on platinum etching (Maa et al. (2001) *J. Vacuum Sci. Technol. A: Vacuum, Surfaces, and Films*, 19: 1312-1314) during the oxygen/$CF_4$ RIE process in FIG. 2(F). The surface roughness of the platinum surface is 319 nm in root-mean-square (RMS), 266 nm in average and 1716 nm in maximum with 15.2 µm$^2$ effective area, which is 3.8-times larger than the scanning area. According to the literature survey, the double-layer capacitance of the platinum electrode is about 40-80 µF/cm$^2$ within the reversible hydrogen electrode (RHE) potential limits (Pell et al. (2002) *J. Electroanalyt. Chem.*, 532: 13-23). Therefore, the calculated capacitance is around 104.1-208.2 nF.

Figure 4:
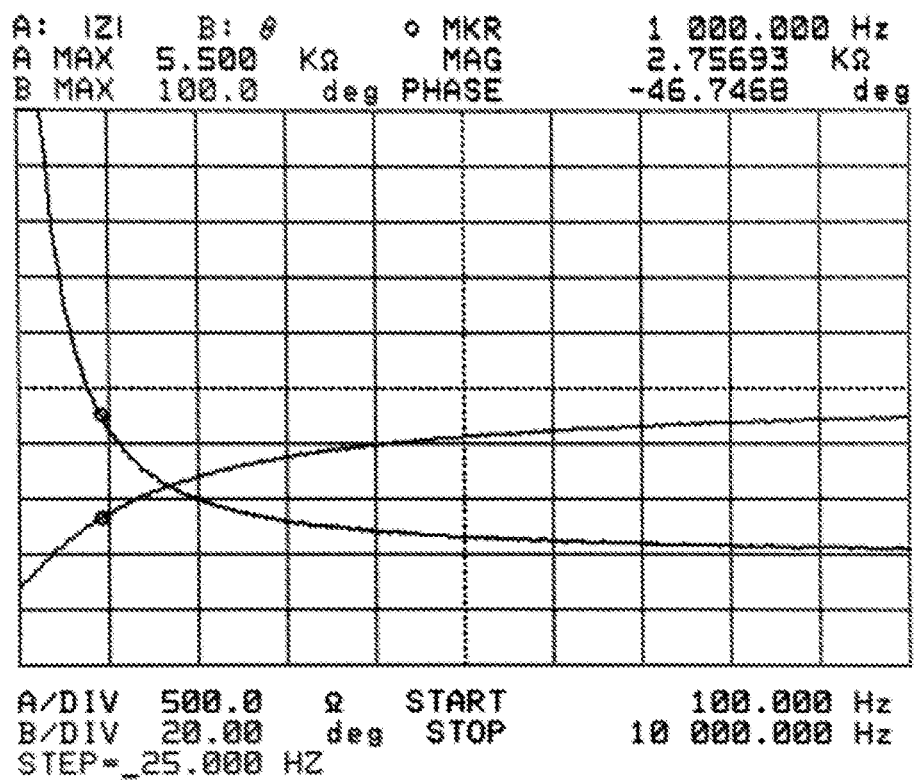
FIG. 4 illustrates the measured impedance of the fabricated electrode array.

FIG. 4 shows the measured impedance of one of the fabricated in a 0.9 wt % physiological sodium chloride solution through an impedance analyzer (HP 4194A). An Ag/AgCl electrode (P-BMP-1, ALA scientific instruments) was used as the reference electrode. The averaged impedance and phase of the large and small grid electrode are 2.35±0.21 KΩ and 2.10±0.11 KΩ, −34.25±8.07° and −27.71±8.27° at 1K Hz with 10 mV input level, respectively (Tested electrode number=27 for each type of the electrode).

Stimulation Test by Multichannel Stimulation System

Figure 6:
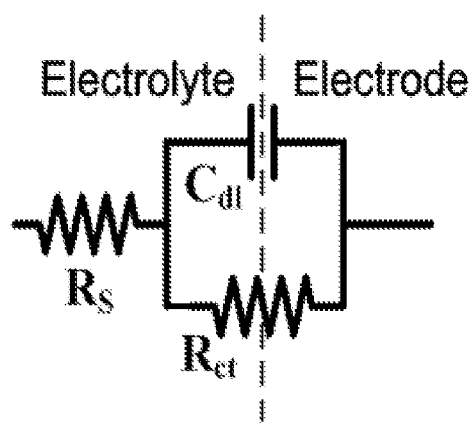
FIG. 6 illustrates a Randles cell model of the electrode-electrolyte interface. $R_{CT}$: charge transfer resistance; $C_{dl}$: double layer capacitance; $R_S$: tissue-solution resistance.
Figure 5:
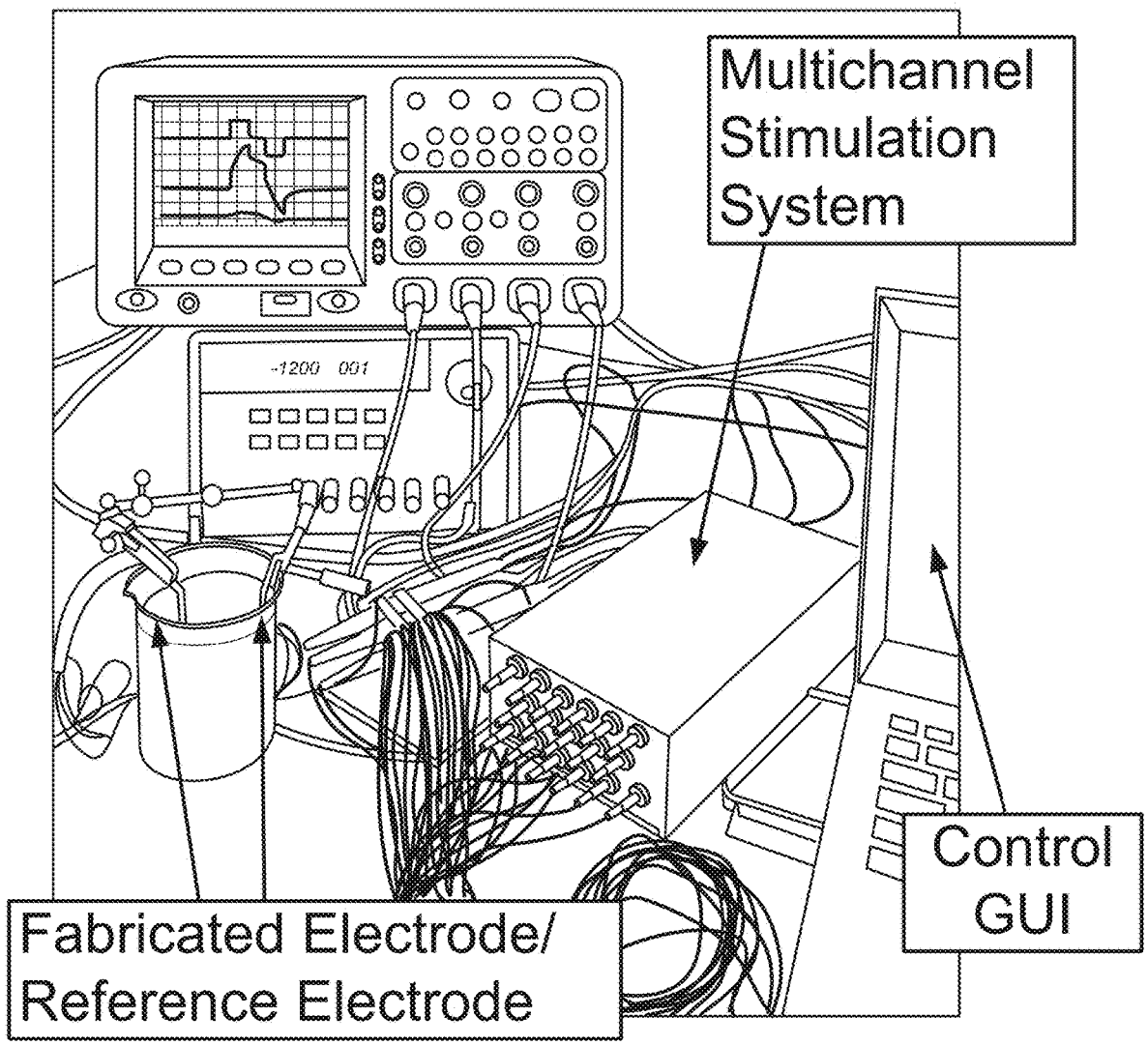
FIG. 5 illustrates the experiment setup. The fabricated electrode was tested by a multichannel stimulation system controlled by a laptop-based GUI.

To validate the electrode performance in practical stimulation, the fabricated electrodes were tested using a multichannel current-mode neural stimulator (L. Yi-Kai, C. Kuanfu, P. Gad, and L. Wentai, (2013) *Biomedical Circuits and Systems, IEEE Transactions on*, 7(6): 761-772, 2013) developed by our group with the same physiological saline solution setup as the impedance analysis, as shown in FIG. 5. FIG. 6 illustrates the Randles cell model of the electrode-electrolyte interface with three elements, which consist of a charge transfer resistance $R_{CT}$, a double layer, capacitance $C_{dl}$, and a tissue-solution resistance $R_S$, respectively.

Figure 7:
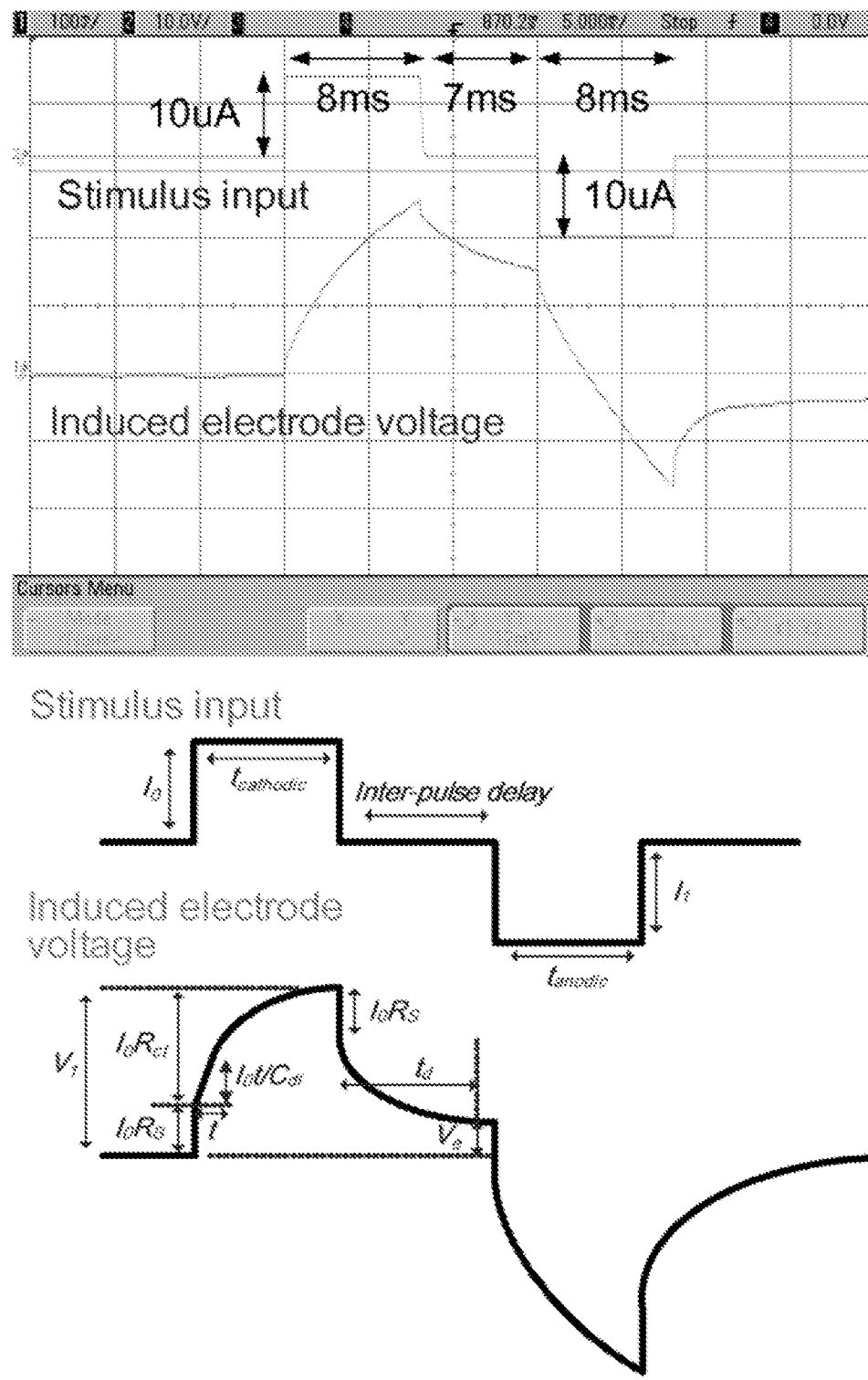
FIG. 7 shows an induced voltage waveform on the electrode during the biphasic current stimulation. A mathematical expression of the voltage waveform is described according to the Randle cell model.

The stimulation result was displayed in FIG. 7. A stimulus biphasic input with 10 μA cathodic/anodic current intensity, 8 ms pulse width and 7 ms inter-pulse delay was injected into to the electrode. A mathematical expression of the voltage waveform is described according to the Randles cell model. At the cathodic rising edge, the input signal can be seen as a very high frequency therefore the $C_{dl}$ becomes a short circuit, all the current will charge the $R_S$ and cause a shape voltage drop. After the evolution comes to the flat cathodic region, the DC current starts to charge the $C_{dl}$ and $R_{CT}$, which results in an exponential-like waveform. At the cathodic falling edge, the $C_{dl}$ is short again, and discharges the $R_S$. After entering the flat anodic region, the DC current starts to discharge the $C_{dl}$ and $R_{CT}$ back to the electrode.

Figure 8:
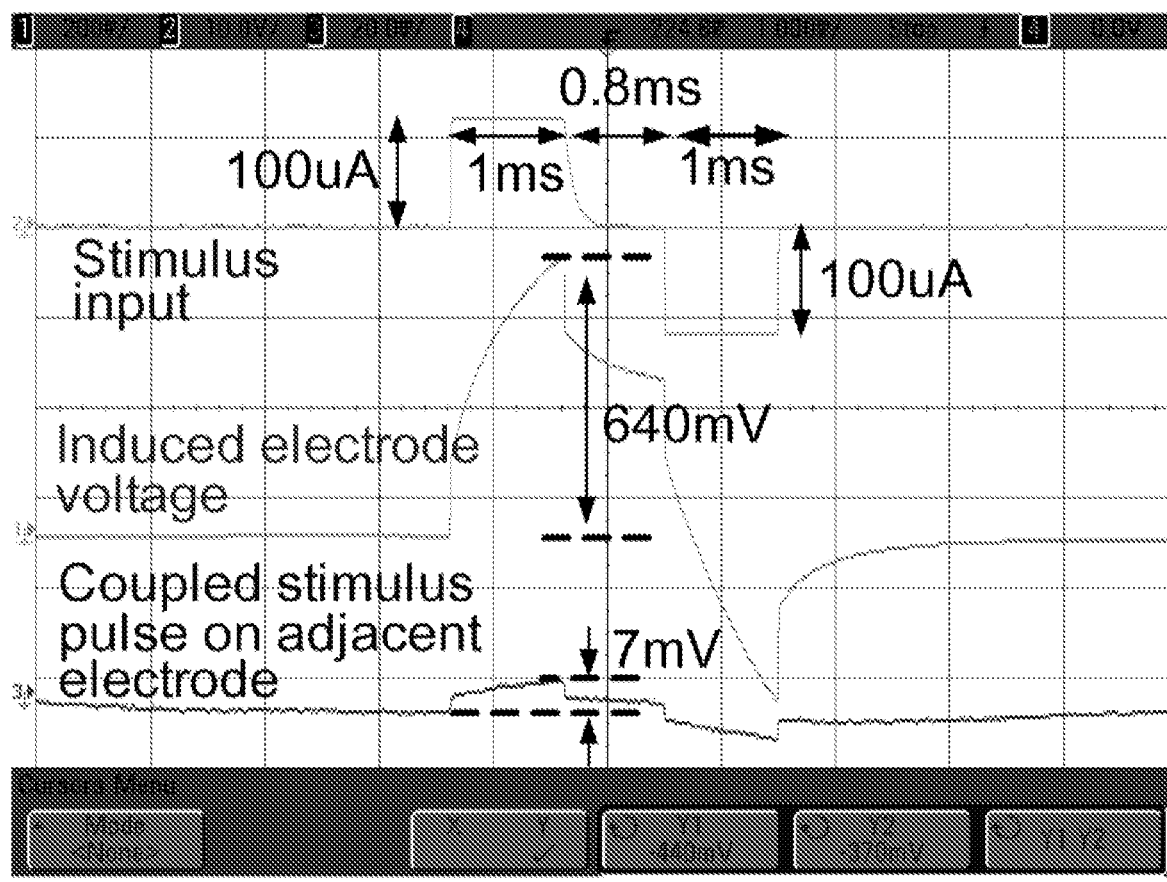
FIG. 8 illustrates the results of a channel isolation test.
Figure 9:
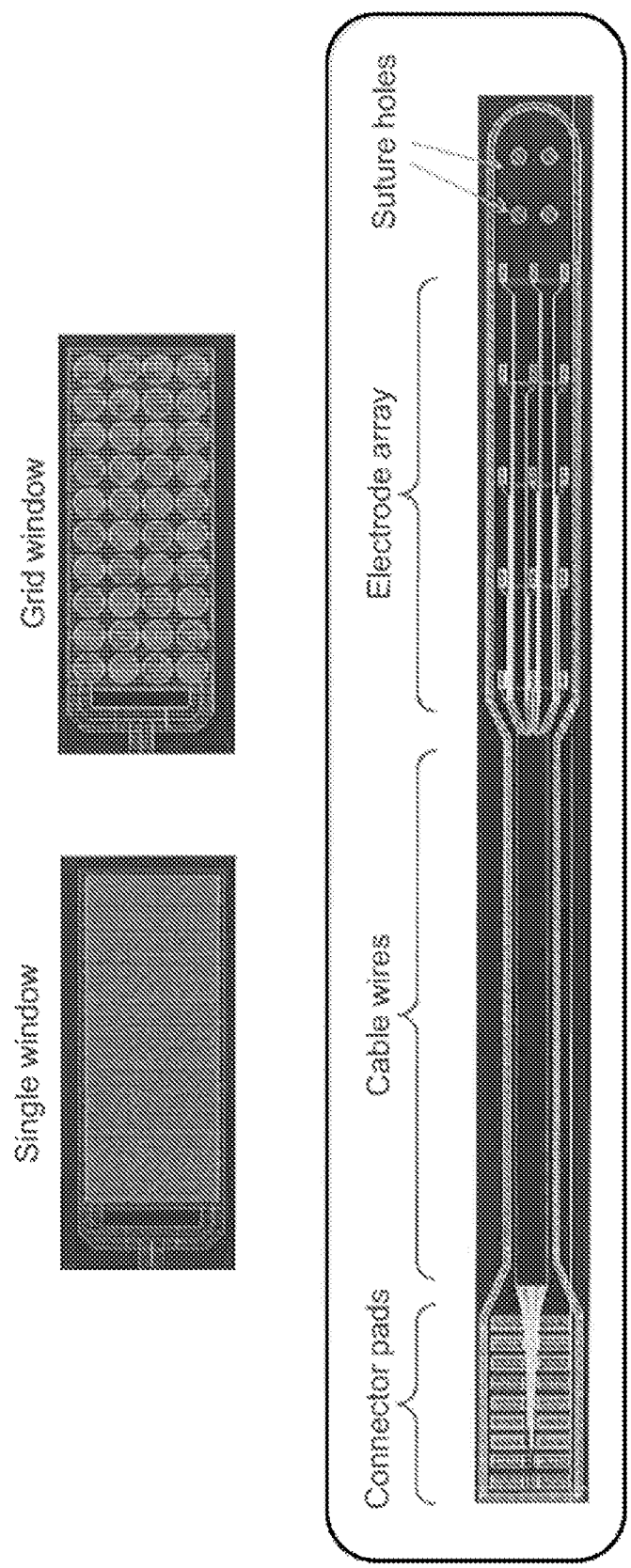
FIG. 9 shows on illustrative, but non-limiting electrode design. In certain embodiments the design can include, but it not limited to 15, 18, 27, and 36 channel designs (e.g., as illustrated in FIG. 10). Illustrative, but non-limiting electrode size is 500 μm×200 μm. The electrode opening can comprise a single window or a grid of windows. In certain embodiments cable wires range in length from 5 mm to 40 mm, or from 10 mm to 30 mm, or from 15 mm to 25 mm.

Coupling effect was evaluated by injecting stimulus current into an electrode, and recording the coupled stimulus signal from a nearest adjacent electrode. As shown in FIG. 8, a maximal electrode voltage of 640 mV in the cathodic phase was induced by a biphasic stimulus current input with 100 μA cathodic/anodic current, 1 ms pulse width and 0.8 ms inter-pulse delay. A 7 mV coupled pulse signal with similar waveform as the stimulus signal was simultaneously recorded from a nearest adjacent electrode. The coupled stimulus signal decayed for −39.22 dB, which shows an ignorable coupled stimulus side effect.

To investigate the validity of the electrode model in detail, we used an impedance acquisition technique based on large signal analysis developed in our group (Yi-Kai Lo et al. (2014) *Conf Proc IEEE Eng Med Biol Soc.* August: 474-477). The parameters of the Randles cell electrode model can be inferred from the pre-determined stimulus parameters, such as pulse width and interpulse delay, and measurement of the resulting transient electrode voltage. The $R_S$ can also be validated by looking into the impedance in very high frequency in FIG. 4, which is closed to the calculation result. The calculated double layer capacitance is also similar to the value from AFM result in Section II. Note that another possible way to evaluate the $C_{dl}$ is using the zero on the impedance plot (FIG. 4) using $R_S$:

$$\text{Zero} = 1/2\pi C_{dl}(R_{CT}\|R_S) \quad (1)$$

$R_{CT}$ might be able to be ignored if $R_{CT} \gg R_S$. A summary of the specifications of the fabricated array are shown in Table 2.

TABLE 2

Illustrative specifications of one electrode array.

| Electrode Materials | Platinum and Polyimide |
|---|---|
| Array Thickness/ Electrode dimension | 8.4 μm/0.5 mm × 0.2 mm |
| Effective Area Factor | 3.8 |
| Surface Roughness RMS | 319 nm |

TABLE 2-continued

Illustrative specifications of one electrode array.

| Electrode Materials | Platinum and Polyimide |
|---|---|
| Impedance@ 1K Hz | 2.35 ± 0.21/ 2.10 ± 0.11 KΩ |
| Phase@ 1K Hz | −34.25 ± 8.07°/ −27.71 ± 8.27° |
| Double Layer Capacitance* | 220 nF |
| Charge Transfer Resistance* | 15 KΩ |
| Tissue Resistance* | 1.9 KΩ |
| Channel Isolation | −39.22 dB |

*Tested in 0.9 wt % physiological sodium chloride solution

CONCLUSION

A flexible polymer electrode array was designed, fabricated, characterized and in-vitro tested using a multichannel stimulator in saline solution for the demonstration of electrical spinal cord stimulation. Low stress polyimide with superior mechanical properties was used to meet the requirements of a good spinal cord implant. Various electrode grid window and array arrangements were proposed to enhance the uniformity of the stimulus charge density and the stimulation pattern combinations. The roughened platinum electrode surface yielded a 3.8× effective area which increased the equivalent double layer capacitance and therefore enhanced the charge transfer capability. The electrode transient waveform was investigated using a lumped Randles cell model with a multichannel stimulation system, which allowed examination of the channel isolation and extraction of the parameters of the electrode model. The model was further validated by various approaches including the large signal analysis technique, AFM and impedance analyzer. The results show that the fabricated electrode is applicable for electrical stimulation with well characterized performance. Combined with a multichannel stimulator, this array completes a full system solution for various applications.

Example 2

Fabrication of a Multi-Electrode Array

The following protocol was used to fabricate the multi-electrode array shown in FIG. 1:

A) Chromium/Aluminum (200 nm/500 nm) layer was deposited by E-beam evaporated deposition (CHA Mark 40) on to a handle silicon wafer.

B) Adhesion promoter (VM-651, HD Microsystems) was applied onto the Chromium/Aluminum layer to create a Si—C bond and provide additional adhesion for the first polyimide layer.

C) A 4.2 μm polyimide (PI-2611, HD Microsystems) was spin-coated onto the wafer, and cured in 350° C. for 30 minutes in a nitrogen-controlled oven to form full cross-link in the polyimide.

D) Positive photoresister AZ4620 was spin-coated onto the wafer. Create the metal pattern by microphotolithography.

E) An oxygen-plasma roughening process was applied to the polyimide layer for 30 seconds to enhance the adhesion performance.

F) Titanium/Platinum (10 nm/200 nm) layer was defined and deposited using E-beam evaporated deposition (CHA Mark 40).

G) Use Lift-off to define the metal pattern from the photoresister.

H) Another 4.2 μm polyimide (PI-2611, HD Microsystems) was spin-coated onto the wafer, and cured in 350° C. for 30 minutes in a nitrogen-controlled oven.

I) A silicon dioxide (200 nm) film was deposited using a DC sputter (Denton Discovery-550) and defined by CHF3/Ar reactive ion etch (RIE) process using a plasma etcher (Oxford Plasmalab-80 Plus).

J) Positive photoresister AZ4620 was spin-coated onto the wafer. Create the electrode pattern by microphotolithography.

K) A pure oxygen plasma process was used to define the array shape as well as exposing the metal layer of electrodes and connector pads.

L) An extra oxygen/$CF_4$ RIE process was utilized to remove the residual layer composed of the silicon containing active ingredient (a-aminopropyltriethoxysilane) which is caused by the Si—C bond promoter. The fluorine etching on platinum in the oxygen/CF4 RIE process roughens the platinum surface.

M) Finally, the electrode arrays were detached from the handle wafer by anodic metal dissolution in a 10 wt % sodium chloride solution. The anodic metal dissolution process dissolved the aluminum, leaving the chrome on the substrate, thus releasing the polyimide electrode arrays.

N) Neural Connector (Omnetics) was soldered onto the arrays. Silicone encapsulation (Sylgard 184) was then applied to seal all the soldering parts and cured in a 120° C. oven for 20 minutes to fully coagulate.

A fluorine added oxygen/$CF_4$ plasma RIE process in step (L) was designed to accomplish two goals in one step: (1) removal of the residual silicon composite from the adhesion promoter Si—C bond; and (2) Roughening the platinum surface by fluorine attack.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of making an electrode array for epidural stimulation of the spinal cord, said array comprising a plurality of electrodes disposed on a flexible polymer substrate, said method comprising:
   depositing a first polymer layer on a support surface and curing said polymer layer to form a cured first polymer layer;
   roughening the surface of said cured first polymer layer;
   using vapor deposition and lift off to deposit metal, metal alloy, and/or metal oxide on the roughed surface of the cured polymer layer to form electrode layers and to define a plurality of electrodes;
   depositing a second polymer layer on said electrodes and curing said polymer layer to form a second cured polymer layer;
   depositing a silicon dioxide film on said second polymer layer and defining features in said film using a reactive ion etch with a plasma etcher;
   coating a positive photoresist coating onto said silicon dioxide film;
   using microphotolithography to create a pattern of electrode contacts;
   using an oxygen plasma process to define a shape of the electrode array as well as exposing a layer of electrode contacts and connector pads on said first polymer layer;
   performing an oxygen/CF4 RIE to roughing a surface of said electrode contacts; and
   detaching the first polymer layer from the support surface to provide an electrode array comprising said first polymer layer forming polymer substrate and a layer of electrode contacts forming said plurality of electrodes.

2. The method of claim 1, wherein said method comprises silicon encapsulation of all soldered parts.

3. The method of claim 1, wherein said first polymer layer and said second polymer layer each comprises a polymer independently selected from the group consisting of polyimide, parylene, polyvinyl chloride (PVC), polyethylene, polyether ether ketone (PEEK), polycarbonate, polyetherimide (PEI), polysulfone, polypropylene, silicone, and polyurethane.

4. The method of claim 3, wherein said polymer is polyimide.

5. The method of claim 1, wherein the polymer layer is deposited by spin coating.

6. The method of claim 1, wherein said electrodes comprise a first layer of titanium underlying a second layer of platinum.

7. The method of claim 1, wherein said support surface comprises a handle silicon wafer.

8. The method of claim 7, wherein said silicon wafer has a chromium/aluminum layer deposited thereon.

9. The method of claim 8, wherein an adhesion promoter is deposited on said chromium/aluminum layer.

10. The method of claim 1, wherein:
    when complete the electrodes of said array are bonded to said first polymer layer so that the electrodes can carry an electrical stimulation signal having a voltage, frequency, and current sufficient to provide epidural stimulation of a spinal cord and/or brain in vivo or in a physiological saline solution, without separation of all or a part of an electrode from the polymer substrate; and/or
    when complete said array is configured so that the electrodes can carry an electrical stimulation signal having a voltage, frequency, and current sufficient to provide epidural stimulation of a spinal cord over a period of at least one week, or over a period of at least two weeks, or over a period of at least one month, or over a period of at least two months, or over a period of at least 3 months, or over a period of at least 6 months, or over a period of at least 1 year in vivo or in a physiological saline solution, without separation of all or a part of an electrode from the polymer substrate.

11. The method of claim 1, wherein said electrode layers comprise one or more metals selected from the group consisting of platinum, titanium, chromium, tungsten, gold, their oxides, and their alloys.

12. The method of claim 1, wherein said electrodes comprise two layers, each layer comprising a different metal.

13. The method of claim 12, wherein when complete the first layer of said electrode is about 10 nm in thickness and the second layer of said electrode is about 200 nm in thickness.

14. The method of claim 1, wherein when complete each electrode comprising a plurality of electrodes comprising said array is individually connected to a corresponding connection point on an electrical connector.

15. The method of claim 1, wherein when complete the electrodes comprising said electrode array are disposed between said first polymer layer and said second polymer layer, said second polymer layer comprising a plurality of openings through which said electrodes are exposed.

16. The method of claim 15, wherein a silicon dioxide layer is present on top of said second polymer layer.

17. The method of claim 15, wherein groups of said openings are localized over each electrode.

18. The method of claim 15, wherein electrodes comprising said array, when complete protrude above a top surface of said second polymer layer.

19. The method of claim 15, wherein electrodes comprising said array when complete are disposed lower than a top surface of said second polymer layer.

20. The method of claim 15, wherein electrodes comprising said array when complete are substantially even with A top surface of said second polymer layer.

21. The method of claim 1, wherein the electrode surfaces are roughened to provide a surface area that is at least 2 times the projected surface area, or at least 3 times the projected surface area, or about 3.8 times the projected surface area.

22. The method of claim 1, wherein:
the thickness of said polymer substrate ranges from about 1 μm up to about 900 μm; and
the thickness of said second polymer substrate, when present, ranges from about 1 μm up to about 900 μm.

23. The method of claim 1, wherein said electrode array, when complete, comprises:
a substantially continuous polyimide polymer substrate;
a plurality of electrodes said electrodes comprising a first layer of titanium and a second layer of platinum disposed on top of said polymer substrate;
a second polyimide polymer layer disposed on top of said electrodes, where said second polyimide layer comprises a plurality of openings through which said electrodes are exposed.

24. The method of claim 23, wherein said polymer substrate and said second polymer layer range in thickness from about 4 μm to about 8 μm.

25. The method of claim 1, wherein said array comprises at least about 6 different electrodes.

26. The method of claim 1, wherein electrodes comprising said array are spaced along a longitudinal axis by a distance ranging from about 0.5 mm up to about 6 mm.

27. The method of claim 1, wherein
the contact surfaces of electrodes comprising said array, are substantially regular polygons and have an average maximum diameter ranging from about 3 μm up to about 150 μm, or from about 5 μm up to about 100 μm, or from about 5 μm up to about 80 μm, or from about 5 μm up to about 60 μm, or from about 10 μm up to about 50 μm, or from about 15 μm up to about 50 μm, or from about 20 μm up to about 45 μm or 50 μm, or from about 25 μm up to about 45 μm or 50 μm, or from about 30 μm up to about 45 μm or 50 μm, or from about 35 μm up to about 45 μm or 50 μm; or
the contact surfaces of electrodes comprising said array, have a major and minor axis where the dimensions of the major and minor axis independently range from about 3 μm up to about 150 μm, or from about 5 μm up to about 100 μm, or from about 5 μm up to about 80 μm, or from about 5 μm up to about 60 μm, or from about 10 μm up to about 50 μm, or from about 15 μm up to about 50 μm, or from about 20 μm up to about 45 μm or 50 μm, or from about 25 μm up to about 45 μm or 50 μm, or from about 30 μm up to about 45 μm or 50 μm, or from about 35 μm up to about 45 μm or 50 μm.

28. The method of claim 27, wherein the contact surface of electrodes comprising said array is about 0.5 mm by 0.2 mm.

29. The method of claim 1, wherein, when complete, the electrodes comprising said array have an effective area factor of at least 2.

30. The method of claim 1, wherein, when complete:
the impedance of said electrode array at 1 KHz is no more than about 5K ohm; and/or
the phase of said array at 1 KHz is no more than 50 degrees; and/or
the double layer (DL) capacitance is at least about 50 nF; and/or
the charge transfer (CT) resistance is no more than about 100K ohm; and/or
the tissue resistance of the complete array is no more than about 5K ohm; and/or
the electrode array provides channel isolation of at least about −20 dB.

31. The method of claim 1, wherein electrodes comprising said electrode array are spaced along a longitudinal axis by a distance ranging from about 0.2 mm up to about 15 mm.

32. The method of claim 1, further comprising attaching electrical correctors to the array electrodes.

33. The method of claim 1, wherein said roughening the surface of said cured first polymer layer is by use of an oxygen-plasma process.

* * * * *